(12) United States Patent
Edelman et al.

(10) Patent No.: US 9,040,092 B2
(45) Date of Patent: May 26, 2015

(54) MATERIALS AND METHODS FOR ALTERING AN IMMUNE RESPONSE TO EXOGENOUS AND ENDOGENOUS IMMUNOGENS, INCLUDING SYNGENEIC AND NON-SYNGENEIC CELLS, TISSUES OR ORGANS

(75) Inventors: Elazer R. Edelman, Brookline, MA (US); Helen Marie Nugent, Needham, MA (US); Heiko Methe, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/570,320

(22) Filed: Aug. 9, 2012

(65) Prior Publication Data

US 2013/0177600 A1 Jul. 11, 2013

Related U.S. Application Data

(63) Continuation of application No. 13/330,099, filed on Dec. 19, 2011, now abandoned, which is a continuation of application No. 11/918,908, filed as application No. PCT/US2006/015555 on Apr. 21, 2006, now abandoned.

(60) Provisional application No. 60/673,419, filed on Apr. 21, 2005, provisional application No. 60/673,417, filed on Apr. 21, 2005, provisional application No. 60/682,217, filed on May 18, 2005.

(51) Int. Cl.
| | |
|---|---|
| A61K 35/12 | (2006.01) |
| A61K 35/28 | (2006.01) |
| A61K 35/26 | (2006.01) |
| A61K 35/44 | (2006.01) |
| A61K 39/00 | (2006.01) |
| C12N 5/071 | (2010.01) |
| A61K 9/00 | (2006.01) |
| A61K 45/06 | (2006.01) |

(52) U.S. Cl.
CPC ............... *A61K 35/44* (2013.01); *A61K 39/001* (2013.01); *A61K 2035/122* (2013.01); *C12N 5/069* (2013.01); *C12N 2533/54* (2013.01); *A61K 9/00* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,418,691 A | 12/1983 | Yannas et al. |
| 4,732,155 A | 3/1988 | Zetter et al. |
| 4,787,900 A | 11/1988 | Yannas |
| 4,820,626 A | 4/1989 | Williams et al. |
| 5,037,378 A | 8/1991 | Muller et al. |
| 5,202,120 A | 4/1993 | Silver et al. |
| 5,399,665 A | 3/1995 | Barrera et al. |
| 5,455,039 A | 10/1995 | Edelman et al. |
| 5,527,532 A | 6/1996 | Edelman et al. |
| 5,540,928 A | 7/1996 | Edelman et al. |
| 5,567,612 A | 10/1996 | Vacanti et al. |
| 5,575,815 A | 11/1996 | Slepian et al. |
| 5,716,404 A | 2/1998 | Vacanti et al. |
| 5,736,372 A | 4/1998 | Vacanti et al. |
| 5,739,113 A | 4/1998 | Lee |
| 5,759,830 A | 6/1998 | Vacanti et al. |
| 5,766,584 A | 6/1998 | Edelman et al. |
| 5,770,193 A | 6/1998 | Vacanti et al. |
| 5,770,417 A | 6/1998 | Vacanti et al. |
| 5,804,178 A | 9/1998 | Vacanti et al. |
| 5,843,156 A | 12/1998 | Slepian et al. |
| 5,855,610 A | 1/1999 | Vacanti et al. |
| 5,879,713 A | 3/1999 | Roth et al. |
| 5,914,268 A | 6/1999 | Keller et al. |
| 6,068,837 A | 5/2000 | Shockley et al. |
| 6,139,574 A | 10/2000 | Vacanti et al. |
| 6,140,039 A | 10/2000 | Naughton et al. |
| 6,156,572 A | 12/2000 | Bellamkonda et al. |
| 6,281,015 B1 | 8/2001 | Mooney et al. |

(Continued)

FOREIGN PATENT DOCUMENTS

| | | |
|---|---|---|
| EP | 0 341 006 | 11/1989 |
| EP | 0 518 389 | 12/1992 |

(Continued)

OTHER PUBLICATIONS

Babaei, et al., "Role of Nitric Oxide in the Angiogenic Response in Vitro to Basic Fibroblast Growth Factor," Circ. Res., 82:1007-1015 (1998).

(Continued)

*Primary Examiner* — Michail Belyavskyi
(74) *Attorney, Agent, or Firm* — K&L Gates LLP

(57) ABSTRACT

Disclosed herein are materials and methods for modulating an immunologically adverse response to an exogenous or endogenous immunogen, including a cell, tissue, or organ associated immunogen. An implantable material comprising cells, such as but not limited to endothelial cells, anchored or embedded in a biocompatible matrix can modulate an adverse immune or inflammatory reaction to exogenous or endogenous immunogens, including response to non-syngeneic or syngeneic cells, tissues or organs, exogenous immunogens or stimuli, as well as ameliorate an autoimmune condition. The implantable material can be provided prior to, coincident with, or subsequent to occurrence of the immune response or inflammatory reaction. The implantable material can induce immunological acceptance in a transplant patient, reduce graft rejection and reduce donor antigen immunogenicity.

13 Claims, 12 Drawing Sheets

(56) References Cited

U.S. PATENT DOCUMENTS

| | | | |
|---|---|---|---|
| 6,290,729 | B1 | 9/2001 | Slepian et al. |
| 6,309,635 | B1 | 10/2001 | Ingber et al. |
| 6,328,762 | B1 | 12/2001 | Anderson et al. |
| 6,348,069 | B1 | 2/2002 | Vacanti et al. |
| 6,358,989 | B1 | 3/2002 | Kunz et al. |
| 6,506,398 | B1 | 1/2003 | Tu et al. |
| 6,528,080 | B2 | 3/2003 | Dunn et al. |
| 6,569,441 | B2 | 5/2003 | Kunz et al. |
| 6,615,071 | B1 | 9/2003 | Casscells, III et al. |
| 6,676,971 | B2 | 1/2004 | Goupil et al. |
| 6,723,131 | B2 | 4/2004 | Muschler |
| 6,726,923 | B2 | 4/2004 | Iyer et al. |
| 6,730,298 | B2 | 5/2004 | Griffith-Cima et al. |
| 6,755,853 | B2 | 6/2004 | McKenzie et al. |
| 6,852,537 | B2 | 2/2005 | Hebbel et al. |
| 6,886,568 | B2 | 5/2005 | Frondoza et al. |
| 6,911,216 | B1 | 6/2005 | Roth et al. |
| 7,011,677 | B2 | 3/2006 | Wallace et al. |
| 7,037,332 | B2 | 5/2006 | Kutryk |
| 2001/0036451 | A1 | 11/2001 | Goupil et al. |
| 2002/0049495 | A1 | 4/2002 | Kutryk et al. |
| 2002/0061303 | A1 | 5/2002 | Singh |
| 2002/0077694 | A1 | 6/2002 | McKenzie et al. |
| 2002/0090398 | A1 | 7/2002 | Dunn et al. |
| 2003/0163192 | A1 | 8/2003 | Wallace et al. |
| 2004/0047843 | A1 | 3/2004 | Meythaler et al. |
| 2005/0008629 | A1 | 1/2005 | Arm |
| 2005/0106554 | A1 | 5/2005 | Palecek et al. |
| 2007/0088252 | A1 | 4/2007 | Pestotnik et al. |
| 2007/0106244 | A1 | 5/2007 | Mosler et al. |

FOREIGN PATENT DOCUMENTS

| | | |
|---|---|---|
| WO | 93/02188 | 2/1993 |
| WO | 93/14193 | 7/1993 |
| WO | 94/22505 | 10/1994 |
| WO | 95/29713 | 11/1995 |
| WO | 01/62241 | 8/2001 |
| WO | 02/07749 | 1/2002 |
| WO | 02/058588 | 8/2002 |
| WO | 02/062335 | 8/2002 |
| WO | 03/026489 | 4/2003 |
| WO | 03/060062 | 6/2003 |
| WO | 03/083044 | 10/2003 |
| WO | 2004/002549 | 1/2004 |
| WO | 2005/032618 | 4/2005 |
| WO | 2005/072417 | 8/2005 |
| WO | 2005/108559 | 11/2005 |
| WO | 2005/120431 | 12/2005 |
| WO | 2006/050063 | 5/2006 |
| WO | 2006/062871 | 6/2006 |
| WO | 2006/062909 | 6/2006 |
| WO | 2006/062962 | 6/2006 |
| WO | 2006/116357 | 11/2006 |
| WO | 2006/120461 | 11/2006 |
| WO | 2007/001744 | 1/2007 |
| WO | 2007/047425 | 4/2007 |

OTHER PUBLICATIONS

Bernemann, et al., "Improvement of the cryopreservation of 293T-cell seeded 3D collagen scaffolds," Journal of Biomechanics, 39:S383 (2006).

Bjornsson, et al., "Acidic Fibroblast Growth Factor Promotes Vascular Repair," Proc. Natl. Acad. Sci. USA, 88:8651-8655 (1991).

Castellot, et al., "Cultured Endothelial Cells Produce a Heparinlike Inhibitor of Smooth Muscle Cell Growth," J. of Cell Biology, 90:372-379 (1981).

Centra, et al., "Culture of Bovine pulmonary artery endothelial cells on gelfoam blocks," Faseb J., 6(12):3117-3121, (1992).

Clowes, et al., "Kinetics of Cellular Proliferation After Arterial Injury I: Smooth Muscle Growth in the Absence of Endothelium," Lab Invest., 49:327-333 (1983).

Cochlovius, et al., "Therapeutic Antibodies," Modern Drug Discovery, 33-38 (2003).

Conte, et al., "Efficient Repopulation of Denuded Rabbit Arteries With Autologous Genetically Modified Endothelial Cells," Circ., 89:2161-69 (1994).

Conte, et al., "Endothelial Cell Seeding Fails to Attenuate Intimal Thickening in Balloon Injured Rabbit Arteries," J. Vasc. Surg., 21(3):413-421 (Mar. 1995).

Cooke, et al., "Cellular Mechanisms of Atherogenesis and the effects of Nitric Oxide," Curr. Opin. Cardiol., 7:799-804 (1992).

Dodge, et al., "Density-Dependent Endothelial Cell Production of an Inhibitor of Smooth Muscle Cell Growth," J. Cell. Biochem., 53:21-31 (1993).

Edelman, et al., "Effect of Controlled Adventitial Heparin Delivery on Smooth Muscle Cell Proliferation Following Endothelial Injury," Proc. Natl. Acad. Sci (USA), 87:3773-3777 (1990).

Edelman, et al., "Basic Fibroblast Growth Factor Enhances the Coupling of Intimal Hyperplasia and Proliferation of Vasa Vasorum in Injured Rat Arteries," J. Clin. Invest., 89:465-473 (1992).

Edelman, et al., "Contrasting Effects of the Intermittent and Continuous Administration of Heparin in Experimental Restenosis," Circ., 89(2):770-776 (1992).

Edelman, et al., "Perivascular and Intravenous Administration of Basic Fibroblast Growth Factor: Vascular and Solid Organ Deposition," Proc. Natl. Acad. Sci. (USA), 90:1513-1517 (1993).

Edelman, et al., "Protamine and Protamine-Insulins Exacerbate the Vascular Response to Injury," J. Clin. Invest., 91:2308-2313 (1993).

Edelman, et al., "Tissue Engineered Endothelial Cell Implants and Proliferative Vascular Disease," Circ., 92 (8):I-748 (1995).

Ellis, et al., "Effect of 18- to 24-hour Heparin Administration for Prevention of Restenosis After Uncomplicated Coronary Angioplasty," Am. Heart. J., 117(4):777-782 (1989).

Esko, "Animal Cell Mutants Defective in Heparan Sulfate Polymerization," Heparin and Related Polysaccharides, (Lane, Bjork & Lindahl, Eds.), Plenum Press, pp. 97-106 (1992).

Farndale, et al., "Improved Quantitation and Discrimination of Sulphated Glycosaminoglycans by Use of Dimethylmethylene Blue," Biochem. et Biophys. Acta, 883:173-177 (1986).

Fishman, et al., "Endothelial Regeneration in the Rat Carotid Artery and the Significance of Endothelial Denudation in the Pathogenesis of Myointimal Thickening," Lab. Invest, 32(3):339-351 (1975).

Gimbrone, "Culture of Vascular Endothelium," Prog. Hemo. and Thromb., 3:1-28 (1976).

Han, et al, "Heparin/heparin sulfate chelation inhibits control of vascular repair by tissue-engineered endothelial cells," Am. J. Physiology, 273(6):H2586-95 (1997).

Hazinedaroglu et al., "Immediate postimplant hemodialysis through a new 'self-sealing' herparin-bonded polycarbonate/urethane graft," Transplantation Proceedings, 36(9):2599-2602 (2004).

Hirigoyen et al., "Periadventitial delivery of heparin in the prevention of micovenous thrombosis," J. Oral and Maxillofacial Surg., 54(9):1097-1102, (1996).

Jarrell et al., "Use of endothelial monolayer on a vascular graft prior to implantation. Temporal dynamics and compatibility with the operating room." Annals of Surg., 203(6):671-678, (1986).

Lee, et al., "Endothelial Cell Seeding Onto the Extracellular Matrix of Fibroblasts for the Development of a Small Diameter Polyurethane Vessel," ASAIO J., 39(3):M740-M745.

Lehmann, et al., "Paradoxical Increase in Restenosis Rate With Chronic Heparin Use: Final Results of a Randomized Trial," J. Am. Coll. Cardiol., 17(2):181A (Abstract) (1991).

Lidington, et al., "A comparison of primary endothelial cell lines for studies of immune interactions," Transplant Immunol , 7(4):239-246, (1999).

Martin et al. "The role of bioreactors in tissue engineering," Trends in Biochemistry, 22(2):80-86 (2004).

McNamara, et al., "L-Arginine Inhibits Balloon Catheter-Induced Intimal Hyperplasia," Biochem. Biophys. Res. Comm., 193 (1):291-296 (1993).

Mestas, et al., "Of Mice and Not Men: Differences Between Mouse and Human Immunology," 172:2731-2738 (2004).

(56) References Cited

OTHER PUBLICATIONS

Methe, et al., "Matrix embedding alters the immune response against endothelial cells in vitro and in vivo," Circ., 112(9 Supp.):I89-I95, (2005).
Methe, et al., "Cell-matrix contact prevents recognition and damage of endothelial cells in states of heightened immunity," Circ., 114(1 Supp.):I233-I238, (2006).
Moncada, et al., "The L-Arginine-Nitric Oxide Pathway," N. Engl. J. Med., 329(27):2002-2012 (1993).
Montañez, et al., "Comparative Study of Tube Assembly in Three-Dimensional Collagen Matrix and on Matrigel Coats," Angiogenesis, 5:167-172 (2002).
Montesano, et al., "Basic Fibroblast Growth Factor Induces Angiogenesis in Vitro," Proc. Natl. Acad. Sci. USA, 83:7297-7301 (1986).
Nathan, et al., "Perivascular Heparin Delivery Using Biodegradable Polymers," Polymeric Materials Science and Engineering, 70:320-321 (Proceedings of the American Chemical Society, Spring Meeting 1994).
Nathan, et al., "Tissue Engineered Perivascular Endothelial Cell Implants Regulate Vascular Injury," Proc. Natl. Acad. Sci. (USA), 92:8130-8134 (1995).
Nugent, et al., "Vascular Cell-Derived Heparan Sulfate Shows Coupled Inhibition of Basic Fibroblast Growth Factor Binding and Mitogenesis in Vascular Smooth Muscle Cells," Circ. Res., 73(6):1051-1060 (1993).
Nugent, et al., "Local Drug Delivery and Tissue Engineering Regulate Vascular Injury," Cur. Pharm. Des. 3(6):529-544 (1997).
Nugent, et al., "Endothelial implants inhibit intimal hyperplasia after porcine angioplasty," Circ. Res., 84(4):384-391, (1999).
Nugent, et al., "Perlecan is required to inhibit thrombosis after deep vascular injury and contributes to endothelial cell-mediated inhibition of intimal hyperplasia," PNAS, 97(12):6722-6727 (2000).
Nugent, et al., "Endothelial Implants Provide Long-Term Control of Vascular Repair in a Porcine Model of Arterial Injury," J. Surg. Res., 99:228-234 (2001).
Nugent, et al., "Transplanted Endothelial Cells Control Repair in Complex Models of Vascular Injury," Circ., 104(17):II-16-17 (2001).
Nugent, et al., "Practices and Considerations in the Development of an Allogeneic Cellular Transplant," BioPharm, 14(1):1-5 (2001).
Nugent, et al., "Perivascular endothelial implants inhibit intimal hyperplasia in a model of arteriovenous fistulae: A safety and efficacy study in the pig," J. Vasc. Res., 39(6):524-533, (2002).
Parikh, et al., "Endothelial cell delivery for cardiovascular therapy," Adv. Drug Delivery Rev., 42:139-161 (2000).
Pascual, et al., "Restoring the endothelium of cryopreserved arterial grafts: co-culture of venous and arterial endothelial cells," Cryobiology, 49(3):272-285 (2004).
Rahmanian, et al., "Testicular Hyaluronidase Induces Tubular Structures of Endothelial Cells Grown in Three-Dimensional Collagen Gel through a CD44-Mediated mechanism," Int. J. Cancer, 97:601-607 (2002).
Rapraeger, et al., "A Quantative Solid-Phase Assay for Identifying Radiolabeled Glycosaminoglycans in Crude Cell Extracts," Analytical Biochem., 179(2):361-365 (1989).
Reidy, et al., "Factors Controlling Smooth-Muscle Cell Proliferation," Arch. Pathol. Lab. Med., 116:1276-80 (1992).
Reidy, et al., "Neointimal Proliferation: the Role of Basic FGF on Vascular Smooth Muscle Cell Proliferation," Thromb. Haemost., 70(1):172-176 (1993).
Satake, et al., "Angiogenic Stimuli Are Essential for Survival of Vascular Endothelial Cells in Three-Dimensional Collagen Lattice," Biochem. Biopys. Res. Comm., 244:642-646 (1998).
Schwartz, et al., "The Aortic Intima; II. Repair of the Aortic Lining after Mechanical Denudation," Am. J. Pathol., 81:15-42 (1975).
Stone, et al., "Effect of endothelial shear stress on the profession of coronary artery disease, vascular remodeling, and in-stent restenosis in humans: in-vivo 6-month follow-up study," Circ., 108(4):438-444, (2003).
Tufveson, et al., "New Immunosuppressants: Testing and Development in Animal Models and the Clinic: with Special Reference to DSG," Immun. Review, 136: 101-107 (1993).
Westerband, et al., "Immunocytochemical Determination of Cell Type and Proliferation Rate in Human Vein Graft Stenoses," J. Vasc Surg., 25: 64-73 (1997).
Zarge, et al., "Fibrin glue containing fibroblast growth factor type 1 and heparin with autologous endothelial cells reduces intimal hyperplasia in a canine carotid artery balloon injury model," J. Vasc. Surg., 25:840-849 (1997).
Sekiguchi, et al. "Neural stem cells contribute to peripheral nerve repair by coordinated angiogenesis and neurogenesis," Circulation. 116:II_79 (2007).
Zavan, et al. "New 3D hyaluronan-based scaffold for in vitro reconstruction of the rat sciatic nerve," Neurological Research-Neuromyology, 30(2):190-6 (2008).
Galis et al., "Matrix Metalloproteinases in Vascular Remodeling and Atherogenesis: The Good, the Bad and the Ugly," Circ. Res. 90:251-262 (2002).
Huynh et al., "Remodeling of an Acellular Collagen Graft Into a Physiologically Responsive Neovessel," Nature Biotechnology, 17: 1083-1086 (1999).
McGrath et al., "New aspects of vascular remodeling: the involvement of all vascular cell types," Exp. Physiol. 90(4): 469-475 (2005).
Misra et al., "Adventitual remodeling with increased matrix metalloproteinase-2 activity in a porcine arteriovenous polytetrafluorethylene grafts," Kidney Int., 68(6): 2890-2900 (2005).
Nagase et al., "Matrix Metalloproteinases," J. Biol. Chem., 274(31): 21491-21494 (1999).
Whatling et al., "Matrix Management: Assignment Different Roles for MMP-2 and MMP-9 in Vascular Remodeling," Arterioscler. Thromb. Vasc. Biol., 24:10-11 (2004).
Feldman, et al., "Anti-TNFalpha Is Useful in Rheumatoid Arthritis and Crohn's Disease: Analysis of the Mechanism of Action Predicts Utility in Other Diseases," Transplant. Proc., 30: 4126-4127 (1998).

MATERIALS AND METHODS FOR ALTERING AN IMMUNE RESPONSE TO EXOGENOUS AND ENDOGENOUS IMMUNOGENS, INCLUDING SYNGENEIC AND NON-SYNGENEIC CELLS, TISSUES OR ORGANS

CROSS-REFERENCE TO RELATED APPLICATIONS

This application is a continuation of U.S. patent application Ser. No. 13/330,099, filed on Dec. 19, 2011, which is a continuation of U.S. patent application Ser. No. 11/918,908, filed Dec. 19, 2007, which is a U.S. national phase application under 35 U.S.C. §371 of International Patent Application No. PCT/US2006/015555, filed Apr. 21, 2006, which claims priority to and the benefit of U.S. Provisional Patent Application No. 60/673,417, filed Apr. 21, 2005, and U.S. Provisional Patent Application No. 60/682,217, filed May 18, 2005, the entire disclosures of each of which are incorporated by reference herein.

FIELD OF THE INVENTION

This invention is directed to materials and methods for modulating an immunologically adverse response to an exogenous or endogenous immunogen, including a cell-, tissue-, or organ-associated immunogen. For example, the present invention can modulate an adverse immune response or inflammatory reaction to exogenous or endogenous immunogens, including non-syngeneic or syngeneic cells, tissues or organs, as well as ameliorate an autoimmune condition.

BACKGROUND OF THE INVENTION

Research on xenotransplantation has been intensified over the past years to alleviate organ shortage. However, host immune responses present a formidable barrier to transplantation across species. Whereas natural antibodies cause immediate rejection of such discordant transplants, endothelial cell (EC) injury and activation of graft vessel lining EC play a pivotal role in initiating chronic graft rejection. Disruption of the integrity of the endothelial layer is of undoubted importance in numerous conditions, including syngeneic and non-syngeneic tissue transplants as well as infectious, neoplastic, inflammatory and cardiovascular diseases.

Heretofore immunomodulation and transplant acceptance have required reliance on systemically-administered immunosuppressive agents. While such agents permit some degree of transplant acceptance, success is limited and perhaps of more significance, a patient's immune system is thoroughly compromised as a result of such agents. Thus a need still remains for therapeutic materials and treatment paradigms which can achieve immunomodulation absent the toxicity and adverse affects on a patient's immune system.

Similarly, exogenous immunogens or stimuli have posed a clinical challenge. These, too, can result in adverse immunological events or inflammatory reactions which necessitate treatment. Heretofore, clinical management of such adverse events has relied almost exclusively on treatments with pharmaceutical agents which suppress the immune system non-specifically.

Autoimmune diseases and other similar diseases are yet another clinical manifestation of heightened inflammatory reactions or adverse immune responses. Successful management of such diseases has eluded clinicians to date.

An object of the present invention is to provide a tissue engineering solution for achieving immunomodulation without reliance on chemicals or pharmaceuticals which compromise a patient's immune system. This tissue engineering solution can be employed to alter, in a clinically practical manner, an immune response to exogenous and endogenous immunogens, including non-syngeneic as well as syngeneic cell-, tissue- or organ-associated immunogens. Another object of the present invention is to facilitate a patient's acceptance of non-syngeneic as well as syngeneic cells, tissues or organs. Another object of the present invention is to employ this tissue engineering solution to modulate an inflammatory reaction such as that associated with injury and various diseases. Another object is to utilize the materials and methods of the present invention to manage autoimmunity and related diseases.

SUMMARY OF THE INVENTION

The present invention exploits the discovery that cells anchored to and/or embedded within a biocompatible matrix, preferably one having a three-dimensional configuration, can modulate an immunologically adverse response or inflammatory reaction to any exogenous or endogenous immunogen. Immunogen includes any syngeneic or non-syngeneic immunogen, including a cell-, tissue-, or organ-associated immunogen, as well as injury, disease and environmental stimuli.

In one aspect, the present invention is a method of reducing an immune response or an inflammatory reaction. According to this method, a recipient is provided an implantable material comprising a biocompatible matrix and anchored and/or embedded endothelial cells, endothelial-like cells, or analogs thereof. The implantable material is provided to the recipient in an amount sufficient to reduce the immune response or inflammatory reaction in the recipient.

According to the invention, the providing step can occur prior to, coincident with, or subsequent to administration to the recipient of one or more doses of a cell, tissue or organ from a syngeneic or non-syngeneic donor. According to another embodiment, the providing step is prior to, coincident with, or subsequent to occurrence of an immune response or inflammatory reaction. According to another embodiment, the method reduces an immune response or an inflammatory response by modulating immunological memory.

In a related aspect, the present invention is a method of inducing immunological acceptance in a patient. According to this method, the patient is provided an implantable material comprising a biocompatible matrix and anchored and/or embedded endothelial cells, endothelial-like cells, or analogs thereof, prior to, coincident with, or subsequent to transplantation of autograft, xenograft or allograft cells, tissue or organ in an amount effective to induce acceptance in the patient.

Additionally, the present invention is directed to a method of reducing donor antigen immunogenicity. According to this method, an implantable material comprising a biocompatible matrix and anchored and/or embedded endothelial cells, endothelial-like cells, or analogs thereof are presented prior to, coincident with, or subsequent to introduction of the donor antigen to a recipient in an amount effective to reduce donor antigen immunogenicity. According to another embodiment, the donor and recipient are the same. According to a further embodiment, the recipient has an autoimmune disease. According to yet another embodiment, the donor antigen comprises a non-endothelial cell antigen.

According to various other embodiments, the providing step occurs prior to, coincident with, or subsequent to administration to the recipient of an immunosuppressive agent. The immunosuppressive agent can reside in the implantable material.

Moreover, the present invention is also directed to a method of transplanting to a recipient a syngeneic or non-syngeneic cell, tissue or organ transplant. According to this method, a recipient is provided an implantable material comprising a biocompatible matrix and anchored and/or embedded endothelial cells, endothelial-like cells, or analogs thereof, prior to, coincident with, or subsequent to transplantation such that the transplanted syngeneic or non-syngeneic cell, tissue or organ is not rejected by the recipient. According to one embodiment of the method, the transplanted cell, tissue or organ comprises non-endothelial cells.

In another aspect, the present invention is an implantable material comprising a biocompatible matrix and cells anchored thereto and/or embedded therein. According to one currently preferred embodiment, the cells are endothelial cells, endothelial-like cells and/or analogs of either. In certain other embodiments, endothelial-like cells or analogs of the implantable material are non-endothelial cells. According to another embodiment, the cells of the implantable material are autogenic, allogenic, xenogenic or genetically-modified variants of any one of the foregoing cell types. According to a further preferred embodiment, the cells of the implantable material are vascular endothelial cells. According to one embodiment, the implantable material is a solid or non-solid. According to yet another, the implantable material is provided to the recipient by implantation, injection or infusion.

The present invention is also directed to an implantable material for reducing an immune response to a syngeneic or non-syngeneic cell, tissue or organ. According to this aspect of the invention, the implantable material comprises a biocompatible matrix and, anchored thereto and/or embedded therein, endothelial cells, endothelial-like cells, or analogs thereof. According to this aspect of the invention, an effective amount of the implantable material reduces the recipient's immune response to the syngeneic or non-syngeneic cell, tissue or organ. According to one embodiment of this aspect of the present invention, the cell, tissue or organ is that of the recipient suffering from an autoimmune disease.

The invention is also directed to a variation of the above-described implantable material which is useful for reducing an immune response to a non-syngeneic cell, tissue or organ, wherein said implantable material comprises cells, tissue, or organ or a segment thereof anchored to and/or embedded within the biocompatible matrix. An effective amount of this implantable material reduces the recipient's immune response to a non-syngeneic cell, tissue or organ. The non-syngeneic cell, tissue or organ is that of the recipient suffering from an autoimmune disease.

In a further aspect, the present invention is a cell suitable for use with the implantable material of any one of inventions described herein. According to one embodiment, the endothelial-like cell or its analog is a non-endothelial cell. According to another embodiment, the analog is non-natural. According to a further embodiment, the cell, when anchored to and/or embedded within a biocompatible matrix, reduces a recipient's humoral or cellular immune response to a syngeneic or non-syngeneic donor cell, tissue or organ.

According to another embodiment, the cell, when anchored to and/or embedded within a biocompatible matrix, exhibits diminished immunogenicity. According to one embodiment, the cell exhibits diminished immunogenicity by exhibiting reduced expression of MHC or reduced capacity to bind, activate or promote maturation of innate immune cells, when anchored to and/or embedded within a biocompatible matrix, wherein said innate immune cells are selected from the group consisting of NK cells, dendritic, cells, monocytes, and macrophages.

According to another embodiment, the cell, when anchored to and/or embedded within a biocompatible matrix, exhibits reduced expression of costimulatory molecules or adhesion molecules. According to a further embodiment, the cell, when anchored to and/or embedded within a biocompatible matrix and co-cultured with a dendritic cell, inhibits expression by said dendritic cell of HLA-DR, IL12, Toll-like receptor or CD83; promotes uptake of dextran by said dendritic cell; or blocks dendritic cell-induced lymphocyte proliferation; or when co-cultured with adaptive immune cells inhibits proliferation, activation or differentiation of said cells, wherein adaptive immune cells are selected from the group consisting of B-lymphocytes and T-lymphocytes.

In another aspect, the present invention is a cell bank comprising any one of the cells described herein. In a further aspect, the present invention is a bank comprising any one of the implantable materials described herein.

In a further aspect, the present invention is a method of reducing an immune response or an inflammatory reaction resulting from exposure to an exogenous immunogen. According to this method, a recipient is provided with an implantable material comprising a biocompatible matrix and anchored or embedded endothelial cells, endothelial-like cells, or analogs thereof. The implantable material is provided to the recipient in an amount sufficient to reduce the immune response or inflammatory reaction in the recipient resulting from exposure to the exogenous immunogen.

According to one embodiment of this method, the providing step is prior to, coincident with, or subsequent to occurrence of the immune response or inflammatory reaction. According to another embodiment, the exogenous immunogen is naturally occurring. According to a further embodiment, the exogenous immunogen is selected from the group consisting of pharmaceutical agents, toxins, surgical implants, infectious agents and chemicals. According to another embodiment, the exogenous immunogen is an exogenous stimulus selected from the group consisting of environmental stress, injury and exposure.

Figure 1A:
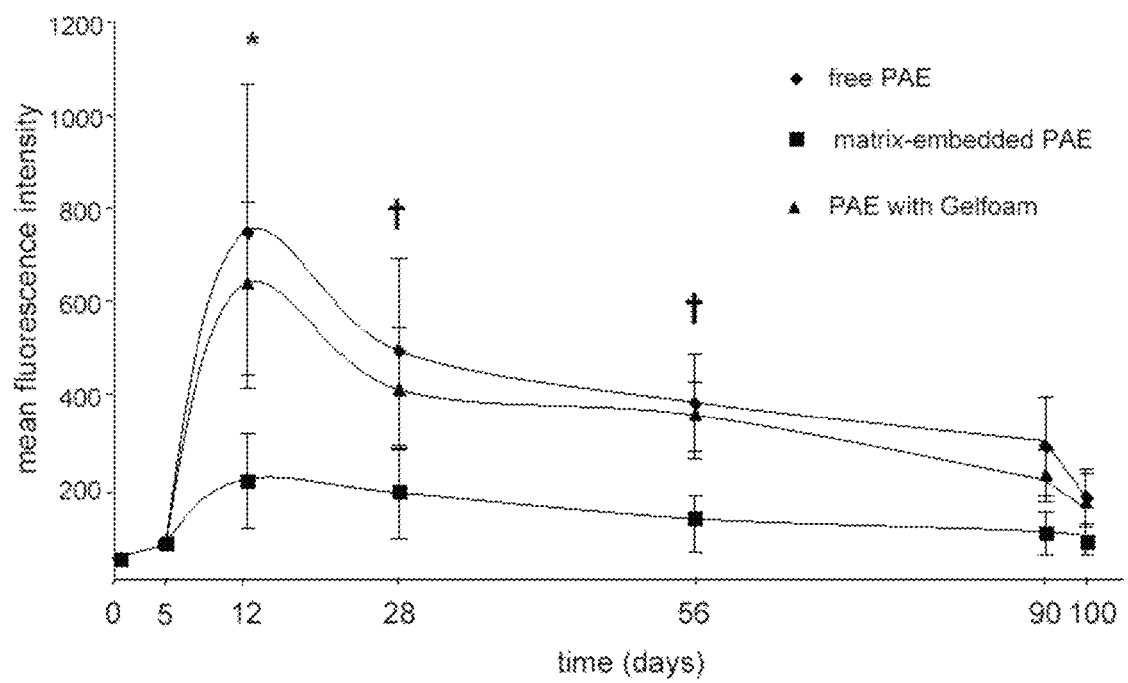
FIGS. 1A, 1B and 1C graphically depict levels of circulating PAE-specific antibodies according to an illustrative embodiment of the invention.

Figures which refer to "embedded" or "matrix-embedded" PAE, HAE or EC mean matrix-anchored and/or matrix-embedded PAE, HAE, EC.

DETAILED DESCRIPTION OF THE INVENTION

Tissue engineering is a promising approach to exploit endothelial cells, endothelial-like cells, or analogs of either as a cellular therapy for diseases accompanied by or typified by adverse immunological components. For example, certain diseases such as but not limited to vascular diseases provoke adverse immunological responses and/or inflammatory reactions. The present invention is based on the discovery that cells such as endothelial cells which are anchored to or embedded in three-dimensional matrices, secrete essential regulatory factors which can ameliorate or otherwise modulate an adverse immunological response.

The implantable material of the present invention was developed on the principals of tissue engineering and represents a novel approach to addressing the herein-described clinical needs. The implantable material of the present invention is unique in that the viable cells anchored to and/or embedded within the biocompatible matrix are able to supply to the site of administration multiple cell-based products in physiological proportions under physiological feed-back control. As described elsewhere herein, the cells suitable for use with the implantable material are endothelial, endothelial-like cells, or analogs of each of the foregoing. Local delivery of multiple compounds by these cells and physiologically-dynamic dosing provide more effective regulation of the processes responsible for modulating an immune response. The implantable material of the present invention can provide an environment which mimics supportive physiology and is conducive to modulation of an immune response.

This is an unexpected discovery since endothelial cells can play a pivotal role in initiation of adverse allo- and xeno-immune responses. Moreover, endothelial cells can activate T-cells through antigen-mediated processes and T-cell activation can modify crucial endothelial cell function, including antigen presentation via activation by cytokines, thereby contributing to an adverse immune response. And, endothelial cells constitutively express class I Major Histocompatibility Complex (MHC) molecules, and IFN-γ can induce endothelial cells to express class II MHC molecules which allows them to provide antigen-dependent signals to $CD8^+$ and $CD4^+$ T-cells through the direct pathway. Endothelial cells also can primarily provide costimulation to T-cells. In addition, the capacity to capture T-cells via endothelial expression of adhesion molecules allows formation of contact regions which furthers the adverse immune response in the form of inflammation. Furthermore, autoimmunity can exacerbate vascular disease, in particular in the form of anti-endothelial cell antibodies. The heightened morbidity of cardiovascular diseases in concert with diabetes mellitus, hypertension and other disease states reflects the increased presence and potentcy of these antibodies.

In contrast, as disclosed herein, matrix-anchored and/or -embedded endothelial cells, when implanted in a host, act as powerful regulators of the immune system as indicated by significant reduction in the expected systemic immune response and/or local inflammation. As exemplified herein, the ability of such cells to ameliorate or modulate immune responsiveness has been demonstrated by comparing the immune response against free versus matrix-anchored and/or -embedded endothelial cells in naïve mice as well as mice with heightened endothelial cell immune reactivity. Matrix-associated endothelial cells as described herein provide immune protection at multiple levels; human and porcine endothelial cells demonstrate a marked reduction in elaborated MHC class molecules; costimulatory molecules; and adhesion molecules when matrix-anchored and/or -embedded as disclosed herein.

Matrix anchoring and/or embedding of endothelial cells can also influence formation of immunological memory as exemplified herein. Whereas reimplantation of free, saline-suspended endothelial cell pellets alone or as pellets situated adjacent to an empty matrix evoked a significant increased humoral and cellular xenoresponse, rechallenging mice with matrix-anchored and/or -embedded endothelial cells led to a reduced lytic ability of splenocytes without enhancing the humoral immune responses. Moreover, a modest shift in the Th1/Th2 balance towards the former was obvious in mice receiving matrix-anchored and/or -embedded xenogeneic endothelial cells.

Thus, introduction of free endothelial cells adjacent to an empty matrix failed to reduce the host immune response indicating the importance of matrix-anchoring and/or -embedding. Failure of anchored and/or embedded endothelial cells to express MHC II, costimulatory, and adhesion molecules upon stimulation could account for the attenuated differentiation of T-cells in effector cells in response to implanted matrix-anchored and/or -embedded xenogeneic endothelial cells. As explained herein, activation of mice splenocytes is muted when exposed to matrix-anchored and/or -embedded xenogeneic endothelial cells in a MHC class II dependent manner.

Overall the isotropic nature of endothelial cells contributes to this unique form of immunomodulation wherein cell anchoring and/or embedding in a suitable matrix provides immunoprotection through isolation or masking of critical antigens. It is well recognized that in vivo endothelial cell function is anchorage- and density-dependent. Previous studies have shown that the endothelial basement membrane (EBM) controls aspects of cell adhesion, spreading, migration, contractility, differentiation, proliferation, protein synthesis and secretion. Furthermore, EBM is altered in many in vivo disease states, from diabetes to glomerulopathy to atherosclerosis. Dysfunction of endothelial cells correlates with changes in basement membrane composition cumulating in the degree of attachment of endothelial cells, and the quality of basement membrane anchoring plays a role for endothelial cells immunobiology.

The present invention is based on the unexpected discovery that anchoring and/or embedding endothelial cells in a suitable biocompatible matrix, such as but not limited to a 3-dimensional collagen-based matrix, can transform xenogeneic endothelial cells into an immunologically non-offending cell phenotype. Such a discovery can now be exploited by the skilled practitioner, following the guidance provided herein, as a tolerance-inducing approach to syngeneic or non-syngeneic therapies such as but not limited to allotransplantation or xenotransplantation as exemplified herein. For example, in a preferred embodiment of the present invention, a clinician can diminish and/or delay rejection by implanting matrix-anchored and/or -embedded endothelial cells prior to transplantation of an allo- or xenograft tissue or organ. For purposes of the present invention, blood is a type of tissue.

Pre-treatment acclimates the recipient's immune system and can result in a reduced, attenuated and/or delayed immune response to a graft. The present invention does not require that the implantable material comprise anchored- and/or embedded cells which are the same as or similar to those ultimately transplanted in the recipient. All that is required is that the implantable material comprising anchored- and/or embedded cells has an immunomodulatory effect when provided to a recipient. In certain circumstances, a single administration prior to or coincident with a transplant can be sufficient. In other circumstances, multiple or serial administrations are preferred. The skilled clinician will recognize such circumstances.

As is well recognized, even transplantation of allogeneic cells is often accompanied by an immune response. A question of much interest is whether this is a constitutive and immutable property of foreign cells or one that can be regulated. The experiments set forth herein demonstrate that the immunogenicity of cells that are normally anchored to basement membranes can be markedly reduced if implanted in a matrix-anchored and/or -embedded state an effect not seen when these same cells were injected in a free state. Other experiments set forth herein investigate the influence of heightened anti-endothelial cell immunity which is a common clinical feature in a variety of autoimmune and endocrinological diseases.

Additionally, certain of the experiments summarized herein demonstrate that serial injections of free porcine aortic endothelial cells (PAE) induced circulating anti-PAE antibodies, elevating immunosensitivity. The response to subsequent PAE injections was even greater than that observed upon first exposure. In contrast, when PAE were implanted in a matrix-anchored and/or -embedded state, the immune response to subsequent exposures was muted and dropped significantly over time. Also, as illustrated below, the initial response to endothelial cells is IgM-mediated, lower than the subsequent IgG response and muted when preceded by serial injections. The IgM response is more evident in naïve than pre-sensitized animals and takes longer to abate after free PAE exposure to than after exposure to matrix-anchored and/or -embedded endothelial cells.

Pre-sensitization of mice with suspensions of free PAE resembles the $IgG_1$-driven anti-endothelial immunity seen in diabetes mellitus, hypertension and autoimmune diseases. The cellular immune response to free and matrix-anchored and/or -embedded cells followed the pattern of humoral immunity. Repeated exposure to antigens resulted in increased formation of memory and subsequently in a more vigorous immune reaction by effector T cells. Hence, the induction of xenoreactive IL-4- and IL-10-producing splenocytes and effector T cells was elevated over time and visible after implantation of free endothelial cells in naïve and pre-sensitized mice. In all mice, cytokine levels correlated linearly and precisely with effector T cell induction further supporting the notion of a Th2-driven cellular response in xenoreactivity and accentuating the immunosilencing aspects of matrix-embedded endothelial cells to activate adaptive immune mechanisms. Damage to implanted endothelial cells correlated with the extent of the immune response elicited. Implanted cells were most profoundly affected after pre-sensitization and with free PAE. The decreased induction of humoral and cellular immune responses in naïve mice receiving matrix-embedded endothelial cells resulted in a lesser degree of damage by host immune cells.

These experiments provide insights into the activation of and damage to endothelial cells, suggesting a pivotal role for cell-matrix contact. The honeycomb-like structure of a currently preferred matrix, Gelfoam, allows endothelial cells to associate with, or anchor to, or embed within its three-dimensional configuration and in certain embodiments, line the internal surfaces of this matrix in a fashion which simulates the appearance of confluent endothelium in quiescent vessels. Thus in certain embodiments, anchoring to and/or embedding endothelial cells within a matrix with the properties of Gelfoam resembles the physiologic three-dimensional state of intact endothelium. The experiments set forth below demonstrate that matrix-anchoring and/or embedding not only protects endothelial cells from host immune reactions but changes the host's perception of endothelial cell immunogenicity.

Thus, during disease for example, phenotypic transformation of endothelial cells dislocated from an intact, matrix-adherent endogenous state to a free state is likely critical to initiation and perpetuation of vascular disease, for example. The teachings herein indicate that endothelial cell detachment precedes expression of adhesion, costimulatory and MHC molecules which is then followed by attraction of immune cells, perpetuating endothelial activation and cell damage. In this regard, the immunobiological and immunoreactive qualities of endothelial cells correlate with morphology and function. Endothelial cells from different vascular beds and divergent basement membrane connectivity demonstrate marked differences in constitutive and inducible expression of adhesion, costimulatory and MHC-molecules. Further, there is growing appreciation that deposition of transitional extracellular matrix proteins such as fibronectin and fibrinogen into the subendothelial matrix as well as detachment of endothelial cells from the basement membrane affects intra-endothelial cell signaling.

As contemplated by the present invention, manipulation of cell phenotype, immunogenicity, and function can be used to tailor the properties of tissue engineered constructs developed in vitro for regenerative purposes; in particular, such a use of the present invention is clinically beneficial since current cell-based therapies are limited by profound host immune reactions. For example, the present invention is particularly useful for treatment of atherosclerotic disease since the presence of activated immune cells and inflammation are key pathophysiologic components. Similarly, heightened anti-endothelial immunity has been identified as a pivotal rate-limiting effect for endothelial cell-based therapies, such as but not limited therapies involving seeding of the interior of a vascular structure with cells or tissue. In contrast, the present invention can be exploited to manage endothelial cell phenotypic shifts which occur in vascular pathology, e.g., via dearrangement of cell-matrix contact, and appropriately targeted therapeutic options can then be implemented in the clinic using the materials and methods of the present invention.

Taken together, the teachings presented herein also demonstrate that features of a matrix such as but not limited to biocompatability, porosity, three-dimensionality, can support the growth of a population of endothelial cells and can modulate the immunogenicity of such cells. Endothelial cells anchored to and/or embedded within a three-dimensional matrix elicited far less activation of host immune mechanisms and were subject to far lower attack and damage from host immune cells. Findings in naïve mice were amplified in hosts with heightened anti-endothelial immunity. In vivo studies presented herein show a marked decrease in the Th2-driven immune response in animals implanted with a matrix such as Gelfoam comprising anchored and/or embedded endothelial cells versus animals injected with free endothelial cells. In order for endothelial cells to activate naïve host T-cells, two signals are required: 1) antigen-presentation in the context of MHC molecules expressed on the donor endothelial cells and 2) a second signal provided by a costimulatory molecule also expressed on the donor endothelial cell surface. Therefore, while not wishing to be bound by theory, one possible explanation for the observed results is that the interaction between a biocompatible matrix and embedded endothelial cells results in a decrease in surface expression of crucial costimulatory, MHC and/or adhesion molecules on the donor endothelial cells. Indeed, in vitro analysis of critical adhesion, MHC-II and co-stimulatory molecule expression on both PAE and HAE (human aortic endothelial cells) show a matrix-anchored and/or embedded dependent profile. The expression profiles of adhesion (E-selectin, P-selectin, ICAM-1, VCAM-1, and CD58), costimulatory (CD40, CD80, CD86) and MHC-II molecules were all reduced in endothelial cells anchored to and/or embedded with a Gelfoam matrix as compared to the same endothelial cells grown on standard tissue culture plates. P-selectin, E-selectin and VCAM-1 are closely associated with T-cell recruitment at sites of immune inflammation. Because antigen presentation to CD4+ T-cells via MHC class II molecules is essential for host immune recognition in the setting of non-vascularized xenogeneic implants, the observed reduced MHC-II expression on matrix-anchored and/or -embedded endothelial cells translated into a reduced proliferative response of host splenocytes. Furthermore, repeated in vitro exposure of the same splenocytes to endothelial cells grown on tissue culture plates elicited a more vigorous secondary response, whereas there was no increased secondary response and therefore no memory of prior exposure to matrix-anchored and/or -embedded endothelial cells. These in vitro findings correlate with the significantly muted immune reaction observed in rats and mice after implantation and re-challenge with matrix-anchored and or embedded endothelial cells as exemplified herein.

Similarly, a mechanism by which culturing endothelial cells in a biocompatible matrix such as but not limited to Gelfoam affects expression of MHC class II molecules, and subsequent endothelial immunogenicity in vitro, was further elucidated by investigating intracellular signaling pathways. Endothelial expression of MHC class II molecules is induced by proinflammatory cytokines (e.g. interferon (IFN)-γ) that are secreted by activated immune cells (e.g. T-cells). Binding of proinflammatory cytokines to their receptors on endothelial cells initiates an intracellular signaling cascade resulting in phosphorylation of Janus protein tyrosine kinase (e.g. JAK-1 and 2) and signal transducer and activators of transcription (e.g. STAT-1). Activation of JAK and STAT are usually tightly regulated within a target cell. As set forth below, detailed in vitro analyses demonstrated differences in IFN-γ induced intracellular signaling pathways between endothelial cells grown to confluence on tissue culture plates as compared to those anchored to and/or embedded or within Gelfoam matrices. Gelfoam-embedded HAE exhibited lower rates of STAT-phosphorylation and activation of the crucial interferon-regulatory factor-1 (IRF-1) with no change in surface IFN-γ receptor expression. Lower rates of JAK activation were also seen upon stimulation of HAE in Gelfoam with IFN-γ.

Upon further investigation, it was observed that non-IFN-γ stimulated HAE grown on a Gelfoam matrix expressed significantly higher levels of the counteracting inhibitory molecule, Suppressor of Cytokine Signaling (SOCS)-1 and 3, than HAE grown on tissue culture plates. One explanation therefore for the muted IFN-γ induced intracellular signaling in Gelfoam-embedded HAE is that the increased levels of SOCS-1 and 3 resulted in an increase in the threshold for cytokine-induced activation of endothelial cells.

In a currently preferred embodiment, the implantable material of the present invention comprising anchored and/or embedded endothelial cells is implanted at any non-luminal site. Thus, immediate exposure of the donor cells to the host circulation is not required. Recent evidence has demonstrated the importance of the soluble endothelial factor $CX_3CL1$ (fractalkine) for attraction of immune cells (i.e., natural killer cells) and surface expressed forms of fractalkine for adherence of those immune cells. Given that only modest cellular infiltration in and around implantation sites of xeno- and allogeneic matrix-anchored and/or embedded endothelial cells was observed, release of soluble and surface expression of fractalkine on HAE was quantified. As illustrated in experiments set forth below, matrix-anchored and/or embedded endothelial cells showed reduced secretion and down-regulation of fractalkine surface expression upon cytokine stimulation as compared to HAE grown on tissue culture plates. This resulted in significantly less adherence of human natural killer cells to matrix-anchored and/or embedded HAE in vitro.

Taken together, the changes in intracellular signaling, increased levels of SOCS-1 and 3 (resulting in attenuated expression of MHC-II molecules and subsequent T-cell activation) as well as reduced secretion and surface expression of fractalkine in matrix-anchored and/or embedded endothelial cells as compared to cells grown on tissue culture plates indicated an altered endothelial cell immunogenicity attributable to matrix-embedding.

Cell Source.

As described herein, the implantable material of the present invention comprises cells which can be syngeneic, allogeneic, xenogeneic or autologous. In certain embodiments, a source of living cells can be derived from a suitable donor. In certain other embodiments, a source of cells can be derived from a cadaver or from a cell bank.

In one currently preferred embodiment, cells are endothelial cells. In a particularly preferred embodiment, such endothelial cells are obtained from vascular tissue, preferably but not limited to arterial tissue. As exemplified below, one type of vascular endothelial cell suitable for use is an aortic endothelial cell. Another type of vascular endothelial cell suitable for use is umbilical cord vein endothelial cells. And, another type of vascular endothelial cell suitable for use is coronary artery endothelial cells. Yet other types of vascular endothelial cells suitable for use with the present invention include pulmonary artery endothelial cells and iliac artery endothelial cells.

In another currently preferred embodiment, suitable endothelial cells can be obtained from non-vascular tissue. Non-vascular tissue can be derived from any tubular anatomical structure as described elsewhere herein or can be derived from any non-vascular tissue or organ.

In yet another embodiment, endothelial cells can be derived from endothelial progenitor cells or stem cells; in still another embodiment, endothelial cells can be derived from progenitor cells or stem cells generally. In a preferred embodiment, the cells can be progenitor cells or stem cells. In other preferred embodiments, cells can be non-endothelial cells that are syngeneic, allogeneic, xenogeneic or autologous derived from vascular or non-vascular tissue or organ. The present invention also contemplates any of the foregoing which are genetically altered, modified or engineered.

In a further embodiment, two or more types of cells are co-cultured to prepare the present implantable material. For example, a first cell can be introduced into the biocompatible matrix and cultured until confluent. The first cell type can include, for example, smooth muscle cells, fibroblasts, stem cells, endothelial progenitor cells, a combination of smooth muscle cells and fibroblasts, any other desired cell type or a combination of desired cell types suitable to create an environment conducive to endothelial cell growth. Once the first cell type has reached confluence, a second cell type is seeded on top of the first confluent cell type in, on or within the biocompatible matrix and cultured until both the first cell type and second cell type have reached confluence. The second cell type may include, for example, endothelial cells or any other desired cell type or combination of cell types. It is contemplated that the first and second cell types can be introduced step wise, or as a single mixture. It is also contemplated that cell density can be modified to alter the ratio of smooth muscle cells to endothelial cells. Similarly, matrices can be seeded initially with a mixture of different cells suitable for the intended indication or clinical regimen.

All that is required of the anchored and/or embedded cells of the present invention is that they exhibit one or more preferred phenotypes or functional properties. The present invention is based on the discovery that a cell having a readily identifiable phenotype (described elsewhere herein) when associated with a preferred matrix can reduce, ameliorate, and/or otherwise modulate an immune response or inflammatory reaction via systemic and/or local effects.

For purposes of the present invention, one such preferred, readily identifiable phenotype typical of cells of the present invention is an altered immunogenic phenotype as measured by the in vitro assays described elsewhere herein. Another readily identifiable phenotype typical of cells of the present invention is an ability to block or interfere with dendritic cell maturation as measured by the in vitro assays described elsewhere herein. Each phenotype is referred to herein as an immunomodulatory phenotype.

Evaluation of Immunomodulatory Functionality:

For purposes of the invention described herein, the implantable material can be tested for indicia of immunomodulatory functionality prior to implantation. For example, samples of the implantable material are evaluated to ascertain their ability to reduce expression of MHC class II molecules, to reduce expression of co-stimulatory molecules, to inhibit the maturation of co-cultured dendritic cells, and to reduce the proliferation of T cells. In certain preferred embodiments, the implantable material can be used for the purposes described herein when the material is able to reduce expression of MHC class II molecules by at least about 25-80%, preferably 50-80%, most preferably at least about 80%; to reduce expression of co-stimulatory molecules by at least about 25-80%, preferably 50-80%, most preferably at least about 80%; inhibit maturation of co-cultured dendritic cells by at least about 25-95%, preferably 50-95%, most preferably at least about 95%; and/or reduce proliferation of lymphocytes by at least about 25-90%, preferably 50-90%, most preferably at least about 90%.

Levels of expression of MHC class II molecules and co-stimulatory molecules can be quantitated using routine flow cytometry analysis, described in detail below. Proliferation of lymphocytes can be quantitated by in-vitro coculturing $^3$[H]-thymidine-labeled CD3+-lymphocytes with the implantable composition via scintillation-counting as described below in detail. Inhibition of dendritic cell maturation can be quantitated by either co-culturing the implantable material with dendritic cells and evaluating surface expression of various markers on the dendritic cells by flow cytometry and FACS analysis, or by measuring dendritic cell uptake of FITC-conjugated dextran by flow cytometry. Each of these methods is described in detail below.

In a typical operative embodiment of the present invention, cells need not exhibit more than one of the foregoing phenotypes. In certain embodiments, cells can exhibit more than one of the foregoing phenotypes.

While the foregoing phenotypes each typify a functional endothelial cell, such as but not limited to a vascular endothelial cell, a non-endothelial cell exhibiting such a phenotype(s) is considered endothelial-like for purposes of the present invention and thus suitable for use with the present invention. Cells that are endothelial-like are also referred to herein as functional analogs of endothelial cells; or functional mimics of endothelial cells. Thus, by way of example only, cells suitable for use with the materials and methods disclosed herein also include stem cells or progenitor cells that give rise to endothelial-like cells; cells that are non-endothelial cells in origin yet perform functionally like an endothelial cell using the parameters set forth herein; cells of any origin which are engineered or otherwise modified to have endothelial-like functionality using the parameters set forth herein.

Typically, cells of the present invention exhibit one or more of the aforementioned phenotypes when present in confluent, near-confluent or post-confluent populations and associated with a preferred biocompatible matrix such as those described elsewhere herein. As will be appreciated by one of ordinary skill in the art, confluent, near-confluent or post-confluent populations of cells are identifiable readily by a variety of techniques, the most common and widely-accepted of which is direct microscopic examination. Others include evaluation of cell number per surface area using standard cell counting techniques such as but not limited to a hemocytometer or coulter counter.

Additionally, for purposes of the present invention, endothelial-like cells include but are not limited to cells which emulate or mimic functionally and phenotypically confluent, near-confluent or post-confluent endothelial cells as measured by the parameters set forth herein.

Thus, using the detailed description and guidance set forth below, the practitioner of ordinary skill in the art will appreciate how to make, use, test and identify operative embodiments of the implantable material disclosed herein. That is, the teachings provided herein disclose all that is necessary to make and use the present invention's implantable materials. And further, the teachings provided herein disclose all that is necessary to identify, make and use operatively equivalent cell-containing compositions. At bottom, all that is required is that equivalent cell-containing compositions are effective to modulate an immune response in accordance with the methods disclosed herein. As will be appreciated by the skilled practitioner, equivalent embodiments of the present composition can be identified using only routine experimentation together with the teachings provided herein.

In certain preferred embodiments, endothelial cells used in the implantable material of the present invention are isolated from the aorta of human cadaver donors. Each lot of cells is derived from a single or multiple donors, tested extensively for endothelial cell purity, biological function, the presence of bacteria, fungi, known human pathogens and other adventitious agents. The cells are cryopreserved and banked using well-known techniques for later expansion in culture for subsequent formulation in biocompatible implantable materials. In other embodiments, living cells can be harvested from a donor or from the patient for whom the implantable material is intended.

Cell Preparation.

As stated above, suitable cells can be obtained from a variety of tissue types and cell types. In certain preferred embodiments, human aortic endothelial cells used in the implantable material are isolated from the aorta of cadaver donors. In other embodiments, porcine aortic endothelial cells (Cell Applications, San Diego, Calif.) are isolated from normal porcine aorta by a similar procedure used to isolate human aortic endothelial cells. Each lot of cells is derived from a single or multiple donors, tested extensively for endothelial cell viability, purity, biological function, the presence of mycoplasma, bacteria, fungi, yeast, known human pathogens and other adventitious agents. The cells are further expanded, characterized and cryopreserved to form a working cell bank at the third to sixth passage using well-known techniques for later expansion in culture and for subsequent formulation as biocompatible implantable material.

The following is an exemplary protocol for preparing endothelial cells suitable for use with the present invention. Human or porcine aortic endothelial cells are prepared in T-75 flasks pre-treated by the addition of approximately 15 ml of endothelial cell growth media per flask. Human aortic endothelial cells are prepared in Endothelial Growth Media (EGM-2, Cambrex Biosciences, East Rutherford, N.J.). EGM-2 consists of Endothelial Cell Basal Media (EBM-2, Cambrex Biosciences) supplemented with EGM-2 which contain 2% FBS. Porcine cells are prepared in EBM-2 supplemented with 5% FBS and 50 µg/ml gentamicin. The flasks are placed in an incubator maintained at approximately 37° C. and 5% $CO_2$/95% air, 90% humidity for a minimum of 30 minutes. One or two vials of the cells are removed from the −160° C.-140° C. freezer and thawed at approximately 37° C. Each vial of thawed cells is seeded into two T-75 flasks at a density of approximately $3\times10^3$ cells per $cm^3$, preferably, but no less than $1.0\times10^3$ and no more than $7.0\times10^3$; and the flasks containing the cells are returned to the incubator. After about 8-24 hours, the spent media is removed and replaced with fresh media. The media is changed every two to three days, thereafter, until the cells reach approximately 85-100% confluence preferably, but no less than 60% and no more than 100%. When the implantable material is intended for clinical application, only antibiotic-free media is used in the post-thaw culture of human aortic endothelial cells and manufacture of the implantable material of the present invention.

The endothelial cell growth media is then removed, and the monolayer of cells is rinsed with 10 ml of HEPES buffered saline (HEPES). The HEPES is removed, and 2 ml of trypsin is added to detach the cells from the surface of the T-75 flask. Once detachment has occurred, 3 ml of trypsin neutralizing solution (TNS) is added to stop the enzymatic reaction. An additional 5 ml of HEPES is added, and the cells are enumerated using a hemocytometer. The cell suspension is centrifuged and adjusted to a density of, in the case of human cells, approximately $1.75\times10^6$ cells/ml using EGM-2 without antibiotics, or in the case of porcine cells, approximately $1.50\times10^6$ cells/ml using EBM-2 supplemented with 5% FBS and 50 mg/ml gentamicin.

Biocompatible Matrix.

According to the present invention, the implantable material comprises a biocompatible matrix. The matrix is permissive for cell growth, and cell anchoring to and/or embedding within the matrix. A particularly preferred matrix is one characterized by a three-dimensional configuration such that anchored and/or embedded cells can create and occupy a multi-dimensional habitat. Porous matrices are preferred. The matrix can be a solid or a non-solid. Certain non-solid matrices are flowable and suitable for administration via injection-type or infusion-type methods. In certain embodiments, the matrix is flexible and conformable. The matrix also can be in the form of a flexible planar form. The matrix also can be in the form of a gel, a foam, a suspension, a particle, a microcarrier, a microcapsule, or a fibrous structure. In certain preferred embodiments, non-solid forms of matrix to which cells are anchored and/or in which cells are embedded can be injected or infused when administered.

One currently preferred matrix is Gelfoam® (Pfizer, New York, N.Y.), an absorbable gelatin sponge (hereinafter "Gelfoam matrix"). Gelfoam matrix is a porous and flexible sponge-like matrix prepared from a specially treated, purified porcine dermal gelatin solution.

According to another embodiment, the biocompatible matrix material can be a modified matrix material. Modifications to the matrix material can be selected to optimize and/or to control function of the cells, including the cells' phenotype (e.g., the immunomodulatory phenotype) as described elsewhere herein, when the cells are associated with the matrix. According to one embodiment, modifications to the matrix material include coating the matrix with attachment factors or adhesion peptides. Exemplary attachment factors include, for example, fibronectin, fibrin gel, and covalently attached cell adhesion ligands (including for example RGD) utilizing standard aqueous carbodiimide chemistry. Additional cell adhesion ligands include peptides having cell adhesion recognition sequences, including but not limited to: RGDY, REDVY, GRGDF, GPDSGR, GRGDY and REDV.

According to another embodiment, the matrix is a matrix other than Gelfoam. Additional exemplary matrix materials include, for example, fibrin gel, alginate, polystyrene sodium sulfonate microcarriers, collagen coated dextran microcarriers, cellulose, PLA/PGA and pHEMA/MMA copolymers (with polymer ratios ranging from 1-100% for each copolymer). According to a preferred embodiment, these additional matrices are modified to include attachment factors, as recited and described above.

According to another embodiment, the biocompatible matrix material is physically modified to improve cell attachment to the matrix. According to one embodiment, the matrix is cross linked to enhance its mechanical properties and to improve its cell attachment and growth properties. According to a preferred embodiment, an alginate matrix is first cross linked using calcium sulfate followed by a second cross linking step using calcium chloride and routine protocols.

According to yet another embodiment, the pore size of the biocompatible matrix is modified. A currently preferred matrix pore size is about 25 µm to about 100 µm; preferably about 25 µm to 50 µm; more preferably about 50 µm to 75 µm; even more preferably about 75 µm to 100 µm. Other preferred pore sizes include pore sizes below about 25 µm and above about 100 µm. According to one embodiment, the pore size is modified using a salt leaching technique. Sodium chloride is mixed in a solution of the matrix material and a solvent, the solution is poured into a mold, and the solvent is allowed to evaporate. The matrix/salt block is then immersed in water and the salt leached out leaving a porous structure. The solvent is chosen so that the matrix is in the solution but the salt is not. One exemplary solution includes PLA and methylene chloride.

According to an alternative embodiment, carbon dioxide gas bubbles are incorporated into a non-solid form of the matrix and then stabilized with an appropriate surfactant. The gas bubbles are subsequently removed using a vacuum, leaving a porous structure.

According to another embodiment, a freeze-drying technique is employed to control the pore size of the matrix, using the freezing rate of the ice microparticles to form pores of different sizes. For example, a gelatin solution of about 0.1-2% porcine or bovine gelatin can be poured into a mold or dish and pre-frozen at a variety of different temperatures and then lyophilized for a period of time. The material can then be cross-linked by using, preferably, ultraviolet light (254 nm) or by adding gluteraldehyde (formaldehyde). Variations in pre-freezing temperature (for example −20° C., −80° C. or −180° C.), lyophilizing temperature (freeze dry at about −50° C.), and gelatin concentration (0.1% to 2.0%; pore size is generally inversely proportional to the concentration of gelatin in the solution) can all affect the resulting pore size of the matrix material and can be modified to create a preferred material. The skilled artisan will appreciate that a suitable pore size is that which promotes and sustains optimal cell populations having the phenotypes described elsewhere herein.

Cell Seeding of Biocompatible Matrix.

The following is a description of one exemplary configuration of a biocompatible matrix. As stated elsewhere, preferred matrices are solid or non-solid, and can be formulated for implantation, injection or infusion.

Pre-cut pieces of a suitable biocompatible matrix or an aliquot of suitable biocompatible flowable matrix are re-hydrated by the addition of EGM-2 without antibiotics at approximately 37° C. and 5% $CO_2$/95% air for 12 to 24 hours. The implantable material is then removed from their re-hydration containers and placed in individual tissue culture dishes. Biocompatible matrix is seeded at a preferred density of approximately $1.5$-$2.0 \times 10^5$ cells ($1.25$-$1.66 \times 10^5$ cells/cm$^3$ of matrix) and placed in an incubator maintained at approximately 37° C. and 5% $CO_2$/95% air, 90% humidity for 3-4 hours to facilitate cell attachment. The seeded matrix is then placed into individual containers (Evergreen, Los Angeles, Calif.) tubes, each fitted with a cap containing a 0.2 μm filter with EGM-2 and incubated at approximately 37° C. and 5% $CO_2$/95% air. The media is changed every two to three days, thereafter, until the cells have reached confluence. The cells in one preferred embodiment are preferably passage 6, but cells of fewer or more passages can be used.

Cell Growth.

A sample of implantable material is removed on or around days 3 or 4, 6 or 7, 9 or 10, and 12 or 13, the cells are counted and assessed for viability, and a growth curve is constructed and evaluated in order to assess the growth characteristics and to determine whether confluence, near-confluence or post-confluence has been achieved. Generally, one of ordinary skill will appreciate the indicia of acceptable cell growth at early, mid- and late time points, such as observation of an exponential increase in cell number at early time points (for example, between about days 2-6 when using porcine aortic endothelial cells), followed by a near confluent phase (for example, between about days 6-8), followed by a plateau in cell number once the cells have reached confluence (for example, between about days 8-10) and maintenance of the cell number when the cells are post-confluent (for example, between about days 10-14).

Cell counts are achieved by complete digestion of the aliquot of implantable material with a solution of 0.5 mg/ml collagenase in a HEPES/Ca$^{++}$ solution. After measuring the volume of the digested implantable material, a known volume of the cell suspension is diluted with 0.4% trypan blue (4:1 cells to trypan blue) and viability assessed by trypan blue exclusion. Viable, non-viable and total cells are enumerated using a hemocytometer. Growth curves are constructed by plotting the number of viable cells versus the number of days in culture.

For purposes of the present invention, confluence is defined as the presence of at least about $4 \times 10^5$ cells/cm$^3$ when in an exemplary flexible planar form of the implantable material ($1.0 \times 4.0 \times 0.3$ cm), and preferably about $7 \times 10^5$ to $1 \times 10^6$ total cells per aliquot (50-70 mg) when in an injectable or infusable composition. For both, cell viability is at least about 90% preferably but no less than 80%.

An exemplary embodiment of the present invention comprises a biocompatible matrix and cells suitable for use with any one of the various clinical indications or treatment paradigms described herein. Specifically, in one preferred embodiment, the implantable material comprises a biocompatible matrix and endothelial cells, endothelial-like cells, or analogs of either of the foregoing. In one currently preferred embodiment, the implantable material is in a flexible planar form and comprises endothelial cells, preferably vascular endothelial cells such as but not limited to human aortic endothelial cells and the biocompatible matrix Gelfoam® gelatin sponge (Pfizer, New York, N.Y., hereinafter "Gelfoam matrix").

Implantable material of the present invention comprises cells anchored to and/or embedded within a biocompatible matrix. Anchored to and/or embedded within means securely attached via cell to cell and/or cell to matrix interactions such that the cells withstand the rigors of the preparatory manipulations disclosed herein. As explained elsewhere herein, an operative embodiment of implantable material comprises a near-confluent, confluent or post-confluent cell population having a preferred phenotype. It is understood that embodiments of implantable material likely shed cells during preparatory manipulations and/or that certain cells are not as securely attached as are other cells. All that is required is that implantable material comprise cells that meet the functional or phenotypical criteria set forth elsewhere herein.

The implantable material of the present invention was developed on the principals of tissue engineering and represents a novel approach to addressing the herein-described clinical needs. The implantable material of the present invention is unique in that the viable cells anchored to and/or embedded within the biocompatible matrix are able to supply to the site of administration multiple cell-based products in physiological proportions under physiological feed-back control. As described elsewhere herein, the cells suitable for use with the implantable material are endothelial, endothelial-like cells, or analogs of each of the foregoing. Local delivery of multiple compounds by these cells and physiologically-dynamic dosing provide more effective regulation of the processes responsible for modulating an immune response. The implantable material of the present invention can provide an environment which mimics supportive physiology and is conducive to modulation of an immune response.

Evaluation of Functionality.

For purposes of the invention described herein, the implantable material is tested for indicia of functionality prior to delivery to a recipient. For example, as one determination of suitability, conditioned media are collected during the culture period to ascertain levels of heparan sulfate or transforming growth factor-β1 (TGF-β1) or basic fibroblast growth factor (b-FGF) or nitric oxide which are produced by the cultured endothelial cells. In certain preferred embodiments, the implantable material can be used for the purposes described herein when total cell number is at least about 1, preferably about 2, more preferably at least about $4 \times 10^5$ cells/cm$^3$ of flexible planar form; percentage of viable cells is at least about 80-90%, preferably ≥90%, most preferably at least about 90%; heparan sulfate in conditioned media is at least about 0.1-0.5 preferably at least about 0.23 microg/mL/day. If other indicia are desired, then TGF-β1 in conditioned media is at least about 200-300, preferably at least about 300 picog/ml/day; b-FGF in conditioned media is below about 200 picog/ml, preferably no more than about 400 picog/ml.

Heparan sulfate levels can be quantitated using a routine dimethylmethylene blue-chondroitinase ABC digestion spectrophotometric assay. Total sulfated glycosaminoglycan (GAG) levels are determined using a dimethylmethylene blue (DMB) dye binding assay in which unknown samples are compared to a standard curve generated using known quantities of purified chondroitin sulfate diluted in collection media. Additional samples of conditioned medium are mixed with chondroitinase ABC to digest chondroitin and dermatan sulfates prior to the addition of the DMB color reagent. All absorbances are determined at the maximum wavelength absorbance of the DMB dye mixed with the GAG standard, generally around 515-525 nm. The concentration of heparan sulfate per day is calculated by subtracting the concentration of chondroitin and dermatan sulfate from the total sulfated glycosaminoglycan concentration in conditioned medium samples. Chondroitinase ABC activity is confirmed by digesting a sample of purified chondroitin sulfate. Conditioned medium samples are corrected appropriately if less than 100% of the purified chondroitin sulfate is digested. Heparan sulfate levels may also be quantitated using an ELISA assay employing monoclonal antibodies.

If desired, TGF-β1 and b-FGF levels can be quantitated using an ELISA assay employing monoclonal or polyclonal antibodies, preferably polyclonal. Control collection media can also be quantitated using an ELISA assay and the samples corrected appropriately for TGF-β1 and b-FGF levels present in control media. Nitric oxide (NO) levels can be quantitated using a standard Griess Reaction assay. The transient and volatile nature of nitric oxide makes it unsuitable for most detection methods. However, two stable breakdown products of nitric oxide, nitrate ($NO_3$) and nitrite ($NO_2$), can be detected using routine photometric methods. The Griess Reaction assay enzymatically converts nitrate to nitrite in the presence of nitrate reductase. Nitrite is detected colorimetrically as a colored azo dye product, absorbing visible light in the range of about 540 nm. The level of nitric oxide present in the system is determined by converting all nitrate into nitrite, determining the total concentration of nitrite in the unknown samples, and then comparing the resulting concentration of nitrite to a standard curve generated using known quantities of nitrate converted to nitrite.

Also, any one or more of the foregoing assays can be used alone or in combination as a screening assay for identifying a cell as suitable for use with the implantable material of the present invention.

While the earlier-described preferred immunomodulatory phenotype can be assessed using one or more of the optional quantitative heparin sulfate, TGF-β1, NO and/or b-FGF functional assays described above, implantable material can be evaluated for the presence of one or more preferred immunomodulatory phenotypes as follows. For purposes of the present invention, one such preferred, readily identifiable phenotype typical of cells of the present invention is an altered immunogenic phenotype as measured by the in vitro assays described below. Another readily identifiable phenotype typical of cells of the present invention is an ability to block or interfere with dendritic cell maturation as measured by the in vitro assays described below. Each phenotype is referred to herein as an immunomodulatory phenotype and cells exhibiting such a phenotype have immunomodulatory functionality.

Evaluation of Immunomodulatory Functionality:

For purposes of the invention described herein, the immunomodulatory functionality of implantable material can be tested as follows. For example, samples of the implantable material are evaluated to ascertain their ability to reduce expression of MHC class II molecules, to reduce expression of co-stimulatory molecules, to inhibit the maturation of co-cultured dendritic cells, and to reduce the proliferation of T cells. In certain preferred embodiments, the implantable material can be used for the purposes described herein when the material is able to reduce expression of MHC class II molecules by at least about 25-80%, preferably 50-80%, most preferably at least about 80%; to reduce expression of co-stimulatory molecules by at least about 25-80%, preferably 50-80%, most preferably at least about 80%; inhibit maturation of co-cultured dendritic cells by at least about 25-95%, preferably 50-95%, most preferably at least about 95%; and/or reduce proliferation of lymphocytes by at least about 25-90%, preferably 50-90%, most preferably at least about 90%.

Levels of expression of MHC class II molecules and co-stimulatory molecules can be quantitated using routine flow cytometry and FACS-analysis, described in detail below. Proliferation of lymphocytes can be quantitated can be quantitated by in-vitro coculturing $^3$[H]-thymidine-labeled CD3+-lymphocytes with the implantable composition via scintillation-counting as described below in detail. Inhibition of dendritic cell maturation can be quantitated by either co-culturing the implantable material with dendritic cells and evaluating surface expression of various markers on the dendritic cells by flow cytometry and FACS analysis, or by measuring dendritic cell uptake of FITC-conjugated dextran by flow cytometry. Each of these methods is described in detail below.

Also, any one or more of the foregoing assays can be used alone or in combination as a screening assay for identifying a cell as suitable for use with the implantable material of the present invention.

Methods of Use and Clinical Indications:

This invention is directed generally to materials and methods for modulating an immunologically adverse response, including an inflammatory reaction, to an exogenous immunogen or stimulus as well as an endogenous immunogen or stimulus. The invention is also directed to a cell-, tissue-, or organ-associated immunogen. For example, the present invention can modulate an adverse immune response to non-syngeneic or syngeneic cells, tissues or organs and/or ameliorate a pre-existing immune condition such as but not limited to an autoimmune condition. This discussion of implantable materials and methods of use for suitable clinical indications will make reference to the following terms and concepts.

An early phase immune response depends on innate immunity. During an innate immune response, a variety of innate immune mechanisms recognize and respond to the presence of immunogen. Innate immunity is present in all individuals at all times and principally discriminates between self, altered self and non-self. For example, a type of innate immune cell is the Natural Killer (NK) cell, the dendritic cell and the monocyte. The innate immune response is followed by an adaptive immune response, mediated by clonal selection of specific lymphocytes and resulting in a more tailored and long-lasting immune response against the recognized antigen.

The adaptive immune response, or adaptive immunity, is the response of antigen-specific lymphocytes to antigen, including the development of immunological memory. Adaptive immune responses are generated by clonal selection of lymphocytes. Adaptive immune responses are distinct from innate and non-adaptive phases of immunity, which are not mediated by clonal selection of antigen-specific lymphocytes. The adaptive immune response includes both cell-mediated immunity and humoral immunity. For example, an adaptive immune cell is a B-cell or T-cell lymphocyte.

One of the hallmarks of an adaptive immune response is establishment of immunological memory. Immunological memory is the ability of the immune system to respond more rapidly and effectively to immunogens been encountered previously, and reflects the pre-existence of a clonally expanded population of antigen-specific lymphocytes.

Protective immunity can be either cell-mediated immunity or humoral immunity. Humoral immunity is specific immunity mediated by antibodies made in a humoral immune response. Cell-mediated immunity describes any adaptive immune response in which antigen specific T cells play a main role.

Autoimmune diseases are mediated by sustained adaptive immune responses specific for self antigens. Tissue injury results because the antigen is an intrinsic component of the body and consequently effector mechanisms of the immune system are directed at self tissues. Also, since the offending autoantigen can not be removed from the body, the immune response persists, and there is a constant supply of new autoantigen, which amplifies the response.

Although some syngeneic grafts or transplants may be accepted long-term, even syngeneic grafts can be problematic for a recipient. In fact, even when autologous cells are harvested, manipulated ex vivo and returned to the original donor, non-acceptance may occur to some extent. Typically, grafts differing at the MHC or at other genetic loci are rejected in the short term by a recipient T-cell response. When donor and recipient differ at the MHC, for example, the immune response is directed at the non-self MHC molecule or other surface molecules expressed by the graft. Acceptance or rejection of a graft or transplant invokes immune events such as antigen recognition, T-cell activation, T-helper cell recruitment and ultimately graft destruction.

An inflammatory reaction is initiated by a local immune response. Acute inflammation is an early transient episode, while chronic inflammation persists such as during autoimmune responses. Inflammation reflects the effects of cytokines on local blood vessels. Cytokines have important effects on the adherent properties of the blood vessel endothelium, causing circulating leukocytes to stick to the endothelial cells of the blood vessel wall and migrate through the wall. Later-stage inflammatory responses also involve lymphocytes of the adaptive immune response which have been activated by immunogen.

Exemplary methods of treatment and clinical indications are discussed below. This is not intended to be an exhaustive discussion. The present invention contemplates any clinical indication suitable for treatment with the present invention, including any clinical indication typified by or otherwise associated with an immunological event having adverse clinical consequences for a patient.

Syngeneic and Non-syngeneic Transplants: The present invention can be used to reduce or diminish a transplant recipient's adverse response to a cell, tissue and/or organ transplant, whether it be a syngeneic or a non-syngeneic transplant. The present invention can also be used to stabilize or maintain a transplant recipient's acceptance of a cell, tissue or organ transplant, whether it be a syngeneic or a non-syngeneic transplant. As taught herein, modulation of an adverse immune response occurs when implantable material is used as a pre-transplant treatment, coincident treatment or post-transplant treatment. For example, it is contemplated that a pre-treatment can acclimate a recipient's immune system which facilitates later acceptance of the transplant. Similarly, coincident treatment can shorten the time course of physiological events which ultimately result in acceptance and ameliorate any adverse immunological events provoked by the transplant. Post-transplant treatments, whether single or multiple, can perpetuate a state of acceptance and keep adverse immunological events in check if/when such events occur. Clinically, typical indications suitable for treatment with the implantable material of present invention include, but are not limited to, allorejection, xenorejection, ischemia-reperfusion injury associated with transplanted tissues or organs, and repetitive treatment courses. Repetitive treatment courses include, for example, recurrent atherosclerosis at different vessel sites requiring repetitive intervention and repetitive replenishing injections of pancreas islet cells. For purposes of the present invention, blood is a type of tissue and blood transfusion recipients can benefit from treatment with the present invention for all the foregoing reasons. Similarly, immunological-based diseases associated with cell, tissue and/or organ transplants benefit from the treatment paradigms set forth above.

Complement dependent Cytotoxicity: In addition to reducing, modulating or eliminating the innate immune response and/or the adaptive immune response, as outlined above, the implantable material of the present invention can also reduce, modulate or eliminate the severity of the complement cascade and the inflammatory side effects of complement activation. For example, attenuation of the complement cascade using the implantable material or the present invention reduces complement mediated cell lysis of a transplanted tissue or organ, thereby ameliorating transplant dysfunction and extending the duration of successful treatment.

Interventional Therapies: As taught herein, the present invention can modulate the severity or robustness of an already-existing immune response as well as a future response provoked by subsequent earlier exposure(s) to an immunogen. Under such circumstances, implantable material can intervene by blocking escalation of an adverse immune response or diminishing onset of hypersensitivity, respectively. Suppression of a memory response can avoid further physiological insult which can jeopardize a patient's organ health, for example. In the case of an already-existing condition, such as an auto-immune condition, the present invention can quell the devastating effects of unabated immunological assaults on a patient's tissues or organs. In essence, such patients are continuously exposed to offending immunogen and their immune response escalates out-of-control resulting in serious, often fatal, disease sequelae.

While an auto-immune condition can be likened to serial challenges with an offending immunogen, other clinical indications can be considered similarly. For example, as suggested above, a recipient of a syngeneic or non-syngeneic transplant is subject to serial challenges. Replenishment of a transplant, such as kidney islet cells which deteriorate over time, constitutes a serial challenge. Secondary infarctions or secondary vascular injuries can be considered serial challenges. Another example is a disease such as but not limited to vasculitis. Any of the foregoing can be effectively managed using the materials and methods of the present invention.

Supplanting Immunosuppressive Agents: As explained elsewhere herein, it is contemplated that administration of the implantable material of the present invention inhibits sufficiently at least T cell activation such that the need to administer harmful immunosuppressive agents is eliminated or significantly reduced. However, it is also contemplated that a certain class of patients, such as a patient pre-disposed to highly exacerbated immune responses, can be treated with both implantable material and an immunosuppressive agent. The implantable material of the present invention, when administered prior to or coincident with transplantation of syngeneic or non-syngeneic tissue, can permit reduced dosages of immunosuppressive agent, if one is necessary, to manage a potential graft rejection response.

Potent immunosuppressive agents, for example, cyclosporin A, tacrolimus (FK-506), sirolimus (rapamicin), mycophenolate mofetil, leflunomide, glucocorticoids, cytostatics, azathioprine, and prednisone, are administered to a transplant recipient to inhibit T cell activation and increase the probability of graft survival. However, administration of potent immunosuppressive agents increases the risk of cancer and infection and contributes to the risk of other side effects including hypertension, dyslipidemia, hyperglycemia, peptic ulcers, and liver and kidney injuries. The present invention can permit more prudent and less risky dosing regimens of such agents. Additionally, immunosuppressants which are typically administered to an organ recipient can be administered prior to, coincident with and/or subsequent to administration of the implantable material of the present invention. For example, implantable materials can amplify the beneficial effects of immunosuppressants while minimizing the risks of such agents in recipients whose immune system is overstimulated or over-sensitized, perhaps reducing the time in which immunomodulation is actually achieved. It is further contemplated that dosages of immunosuppressants, in certain embodiments, are less than those typically administered in the absence of implantable material, thereby exposing a recipient to less toxic doses of immunosuppressants.

Altering the Time Course of an Immune Response: In a preferred embodiment of the invention, matrix-anchored and/or embedded endothelial cells are administered to diminish or delay an immune or inflammatory response. It is not necessary that the implantable material completely eliminate an immune or inflammatory response to be considered effective. Rather, the material need only alter the time course of a response, such as by reducing the duration of an immune or inflammatory response or by reducing an acute inflammatory response to a chronic inflammatory response. Delaying an immune or inflammatory response allows a coincident or later administered therapy to effectively treat a recipient in the absence of an immune or inflammatory response and/or to increase the duration of transplant acceptance. Thus any delay or reduction in the severity of an adverse immune response is beneficial clinically to a patient.

Furthermore, the implantable material of the present invention can also be used to manage or reduce an immune response and inflammatory reaction associated with any exogenous foreign body or foreign material introduced to a patient, or any form of exogenous stimulus. The present invention contemplates exogenous immunogens which are naturally-occurring. The present invention also contemplates exogenous immunogens, including but not limited to pharmaceutical agents, toxins, surgical implants, infectious agents and chemicals. For purposes of the present invention, an exogenous immunogen can be an exogenous stimulus such as, but not limited to, environmental stress, injury, exposure or any stimulus which provokes an adverse immune response or inflammatory reaction.

For example, synthetic graft materials, such as a synthetic PTFE® arteriovenous graft, or other synthetic surgical materials or prosthetic devices, can induce a foreign body reaction in the host. This type of immune or inflammatory response can also be reduced or eliminated by administering the implantable material of the present invention to the patient prior to or at the time of implanting the synthetic material. Administration subsequent to implantation is also effective. Reducing any foreign body reaction in the host improves the overall function and/or outcome of the treatment.

General Considerations.

In certain embodiments of the invention, additional therapeutic agents are administered prior to, coincident with and/or following administration of the implantable material. For example, cytokines or growth factors can also be incorporated into the implantable material, depending on the clinical indication necessitating the implant, including agents which can mute an immune-related humoral or cellular event, or tissue-associated biochemical cascade. Other types of therapeutic agents include those which can promote the longevity of cells anchored to and/or embedded within the implantable material and/or agents which can delay the bioerosion of an erodible biocompatible matrix post implantation. Any of the foregoing can be administered locally or systemically; if locally, certain agents can be contained within the implantable material or contributed by the cells per se.

Administration Considerations.

As contemplated herein, the implantable material of the present invention can be delivered to or situated at any compatible anatomical site provided that conditions at the site do not cause mechanical-type or physical-type disruption or untimely disintegration of the implantable material, or otherwise compromise the physical integrity or the functionality of the implantable material. For example, the present invention can be situated subcutaneously, perivascularly, or intraperitoneally. One preferred site is a skin pouch. Other preferred sites can be perivascular or non-perivascular. The implantable material can be situated adjacent to or in contact with an organ or a tubular anatomical structure which can be a vascular or non-vascular structure. The present invention can be delivered to any compatible site for purposes of either systemic modulation of a humoral or cellular immune response, or for purposes of local modulation of an inflammatory reaction, or both. Certain preferred embodiments of implantable material can reside at an implantation site for at least about 56-84 days, preferably about at least 7 days, more preferably about at least 14 days, even more preferably about at least 28 days, and most preferably more than about 28 days before it bioerodes.

When ready for delivery to a recipient, the implantable material when in an exemplary flexible planar form, is a 1×4×0.3 cm (1.2 cm$^3$) sterile piece with preferably approximately 5-8×10$^5$ preferably at least about 4×10$^5$ cells/cm$^3$ and at least about 90% viable cells, for example, human aortic endothelial cells derived from a single cadaver donor source, per cubic centimeter in approximately 45-60 ml, preferably about 50 ml, endothelial growth medium (for example, endothelial growth medium (EGM-2) containing no phenol red and no antibiotics. When porcine aortic endothelial cells are used, the growth medium is also EBM-2 containing no phenol red, but supplemented with 5% FBS and 50 µg/ml gentamicin.

In certain embodiments contemplated herein, the implantable material of the present invention is a flowable composition comprising a particulate biocompatible matrix which can be in the form of a gel, a foam, a suspension, a particle, a microcarrier, a microcapsule, or other flowable material. Any non-solid flowable composition for use with an injection-type or infusion-type delivery device is contemplated herein. In certain embodiments, the flowable composition is preferably a shape-retaining composition. An implantable material comprising cells in, on or within a flowable-type particulate matrix as contemplated herein can be formulated for use with any injection-type delivery device ranging in internal diameter from about 22 gauge to about 26 gauge and capable of delivering about 50 mg of flowable composition comprising particulate material containing preferably about 1 million cells in about 1 to about 3 ml.

According to a currently preferred embodiment, the flowable composition comprises a biocompatible particulate matrix such as Gelfoam® particles, Gelfoam® powder, or pulverized Gelfoam® (Pfizer Inc., New York, N.Y.) (hereinafter "Gelfoam particles"), a product derived from porcine dermal gelatin. According to another embodiment, the particulate matrix is Cytodex-3 (Amersham Biosciences, Piscataway, N.J.) microcarriers, comprised of denatured collagen coupled to a matrix of cross-linked dextran.

Endovascular Administration. The flowable composition can also be administered via an intraluminal or endovascular route even though the final deposition site is not intraluminal. For example, the composition can be delivered by any device able to be inserted within the blood vessel. Endoscopic guidance systems may be used to locate the delivery device at the site of administration, including, for example, intravascular ultrasound (IVUS), color Doppler ultrasound, duplex ultrasound, other routine ultrasound, angiography, magnetic resonance angiography (MRA), magnetic resonance imaging (MRI), CT scanning, fluoroscopy to identify the location of a stent and/or other endoscopic guidance systems known in the field. Additionally, the site of administration may be located using tactile palpation.

In one instance, the intraluminal delivery device is equipped with a traversing or penetrating device which penetrates the luminal wall of a blood vessel to reach a non-luminal surface of a blood vessel. The flowable composition is then deposited on the non-luminal surface. It is contemplated herein that a non-luminal, also termed an extraluminal, surface can include any site exterior to a blood vessel or any perivascular surface of a vessel, or can be within the adventitia, media, or intima of a blood vessel, for example. For purposes of this invention, non-luminal or extraluminal means any surface except an interior surface of the lumen. It is also contemplated that deposition within the perivascular space can be accomplished via an intraluminal delivery device and does not require contact with the extraluminal surface of the traversed vessel.

The penetrating devices contemplated herein can permit, for example, a single point of delivery or a plurality of delivery points arranged in a desired geometric configuration to accomplish delivery of the flowable composition to a non-luminal surface of a blood vessel without disrupting an injured or diseased target site. A plurality of delivery points can be arranged, for example, in a circle, a bulls-eye, or a linear array arrangement to name but a few. The penetrating device can also be in the form of a stent perforator, such as but not limited to, a balloon stent including a plurality of delivery points.

Percutaneous Administration. Flowable composition can be delivered via a percutaneous route using a needle, catheter or other suitable delivery device. The flowable composition can be delivered percutaneously coincident with use of a guidance method to facilitate delivery to the site in need of treatment. The guidance step is optional. Endoscopic guidance systems can be used to locate a site of extraluminal administration, for example, including intravascular ultrasound (IVUS), color Doppler ultrasound, duplex ultrasound, other routine ultrasound, angiography, magnetic resonance angiography (MRA), magnetic resonance imaging (MRI), CT scanning fluoroscopy. Additionally, the site of administration can be located using tactile palpation. Upon entry into the perivascular or peritoneal space, for example, the clinician can deposit the flowable composition on any non-luminal surface or at any non-luminal site. The guiding or identifying step is optionally performed and not required to practice the methods of the present invention. In another embodiment, the implantable flowable composition is delivered locally to a surgically-exposed extraluminal site.

Also contemplated is administration by infusion. Infusion can be accomplished as a bolus-type dose or a slower-type, gradual dose. The skilled clinician will recognize the advantages of each and will recognize the circumstances in which to employ one or the other modes of administration. All that is required is routine clinical infusion apparatus.

Experimental Materials and Procedures

Material Preparation and Evaluation.

As described in greater detail elsewhere herein, porcine aortic endothelial cells and human aortic endothelial cells were individually isolated and cultured. The cultured cells were then seeded on a three-dimensional biocompatible matrix, such as Gelfoam, and incubated until the cells reached confluence. The functionality of the endothelial cells anchored to and/or embedded within the matrix was evaluated according to the previously discussed protocols.

Endothelial Cell-Induced Immune Reaction in Rats.

Fifty-four Sprague-Dawley rats received $5 \times 10^5$ porcine aortic endothelial cell transplants in the subcutaneous dorsal space as Gelfoam-embedded cells, saline-suspended cell pellets, or as pellets adjacent to empty Gelfoam. After dorsal incision, a small subcutaneous cavity was built in blunt technique and Gelfoam-embedded cells carefully inserted or cells injected. Empty control Gelfoam matrices were incubated in complete DMEM prior to implantation. Sera were collected serially from 0 to 56 days, aliquoted and stored at −70° C.

Endothelial Cell-Induced Immune Reaction in Mice.

Thirty-six B6-mice received $5 \times 10^5$ porcine aortic endothelial cell implants in the subcutaneous dorsal space as Gelfoam-embedded cells, saline-suspended cell pellets, or as pellets adjacent to empty Gelfoam. Empty control Gelfoam matrices were incubated in complete DMEM prior to implantation. To evaluate the impact of matrix-embedding on immunological memory the same groups of mice were rechallenged with the identical treatment on day 100. Sera were collected serially from 0 to 90 days after each implantation-procedure, aliquoted and stored at −70° C. Four mice of each group were sacrificed on day 28 and day 128 respectively for splenocyte isolation.

Endothelial Cell-Induced Immune Reaction in Serially Challenged Mice.

Porcine aortic endothelial cells (PAE) isolated from Large-White swine aorta were either seeded on Gelfoam as previously described or grown to confluence on polystyrene plates. B6-mice received injections in the subcutaneous dorsal space on days 0, 21, 35 of $5 \times 10^5$ PAE (n=24, pre-sensitized mice) or saline (n=24, naïve mice). On day 42, 12 mice from each group received $5 \times 10^5$ matrix-embedded or free PAE. Host immune reactions and lytic damage of endothelial cells were studied for the following 90 days. Sera were collected serially from days 42 to 132, aliquoted and stored at −70° C. Six mice of each group were sacrificed on day 70, the remaining on day 132 for splenocyte isolation.

Experiments

Endothelial Cells Embedded in a Three-Dimensional Matrix Grow in a Three-Dimensional Pattern.

Scanning electron microscopy was performed to evaluate the growing pattern of endothelial cells grown within a biocompatible matrix. Implantable material comprising endothelial cell anchored to and/or embedded within a Gelfoam matrix were rinsed with PBS, divided into 0.5 cm specimens, fixed with 3% glutaraldehyde (Sigma Chemicals; St. Louis, Mo.) 90 min, and transferred to distilled water. After incubation in 1% OsO4, specimens were rinsed with distilled water and dehydrated in serial solutions of ethanol (30, 50, 75, 80, 85, 90, 95, and 100%) at 15 min intervals, and hexamethyldisilazane (Sigma) (50%, 100%) at 30 min intervals. Specimens were evaporated overnight in 100% HMDS and thereafter coated with gold in a plasma coater (Edwards Coating System, U.K.). Scanning electron microphotographs were obtained at 5-kV acceleration voltage (Stereoscan 240, Cambridge Instruments, U.K.).

Scanning electron microscopy revealed a 3-D growing pattern of porcine aortic endothelial cells along the interstices of the Gelfoam-matrix. Cell viability remained at 95% over the 2-week culture course.

Experimental data indicate that the in-vivo immunoacceptance of Gelfoam-embedded cells is an effect of the three-dimensional growing pattern of endothelial cells in the matrix rather than from the presence of the biocompatible matrix alone. Typically, implanted cells or proteins combined within tissue-engineered biomaterials serve as a source of antigens immuno-stimulating. Yet, the Gelfoam matrix is immunoneutral and itself has no immune protective effect since injection of porcine aortic endothelial cells adjacent to Gelfoam matrix alone evoked the same immune response as free injected endothelial cells. The nature of endothelial cells contributes to this unique form of immunomodulation observed with matrix-embedded cell preparations. In particular, these cells have a sidedness: a basal surface that interacts with basement membrane and superior surface that interacts with flowing blood and cellular elements. Data suggest that endothelial cell function is anchorage- and density-dependent. Systemic diseases like hypertension, alterations in lipid and glucose metabolism or exposure to toxins alter anchorage-dependent regulation and the amplitude and nature of immune responses against the endothelium and phenotypic transformation of intact endothelial cells from matrix-adherent to free contributes to initiation of vascular disease.

Modulation of Surface Molecules Including Co-Stimulatory and Adhesion Molecules.

Expression levels of costimulatory and adhesion molecules on endothelial cells in vitro were quantified by flow cytometry. FITC- and PE-labeled antibodies were used and included mouse anti-porcine P-selectin antibody, mouse anti-porcine CD31 (clone LCI-4), anti-human CD54 (clone 15.2), anti-human CD62E (clone 1.2B6), anti-human CD58 (clone 1C3), anti-human CD80 (clone BB1), anti-human CD86 (clone 2331), anti-human 4-1BB-ligand (PE-labeled, clone C65-485), rat anti-mouse $IgG_1$ (clone A85-1), and anti-mouse IgM (clone R6-60.2), rabbit anti-rat IgG, rabbit anti-human CD40, goat anti-rabbit IgG, mouse anti-human CD106 (clone 1.G11B1), mouse anti-human HLA-DP,DQ, DR (clone CR3/43), mouse anti class I MHC ($IgG_{2a}$), rat anti-mouse $IgG_{2a}$, mouse anti-human ox40-ligand, mouse anti-human Programmed Death Ligand 1 (PD-L1, clone MIH1), anti-human PD-L2 (clone MIH18), and anti-human inducible costimulator ligand (ICOS-ligand, clone MIH12).

Endothelial cell monolayers or endothelial cells embedded in Gelfoam were harvested after culture in complete medium (CD31, CD58, PD-L2, ox40-ligand, MHC-I), stimulated with 100 U/ml TNF-α (CD54, CD80, CD86, CD106, E-selectin, P-selectin) or 200 U/ml TNF-α (ICOS-L) for 24 hours, 10 μg/ml LPS for 24 hours (4-1BB-ligand), 1000 U/ml IFN-γ (MHC-II, CD40), or 100 U/ml IFN-γ and 25 ng/ml TNF-α (PD-L1) for 48 hours. Media were aspirated and cells were washed with PBS. Monolayers incubated in 1.0 mM PBS/EDTA for 5 min, and disrupted by gentle shaking. Gelfoam were digested with collagenase type I, shown to have no effect on expression of surface molecules. Cell-suspensions were washed and $3 \times 10^5$ cells were resuspended in FACS buffer (PBS containing 0.1% BSA and 0.1% sodium azide, Sigma Chemicals; St. Louis, Mo.). Endothelial cells were incubated with primary antibodies for 30 min at 4° C. If necessary, cells were resuspended in FACS buffer and stained with a secondary antibody for 30 min at 4° C. Cells were then washed, fixed in 1% paraformaldehyde, and $10^4$ cells were analyzed by flow cytometry using a FACScalibur instrument and CellQuest software (Becton Dickinson, San Diego, Calif.).

Embedding porcine aortic endothelial cells in a three-dimensional biocompatible matrix altered the expression of surface molecules. Constitutive expression of CD58 was significantly reduced in porcine aortic endothelial cells embedded in Gelfoam compared to CD58 expression of porcine aortic endothelial cells grown on tissue culture polystyrene plates (−60.4%, p<0.002). There was also a significant reduction in upregulation of costimulatory and adhesion molecules, and MHC class II on matrix-embedded porcine aortic endothelial cells compared to porcine aortic endothelial cells grown on polystyrene plates under FACS-analysis (CD80: −64.9%, p<0.002; CD86: −65.4%, p<0.001; CD40: −53.8%, p<0.005; ICAM-1: −68.7%, p<0.001; VCAM-1: −53.9%, p<0.005; E-selectin: −71.8%, p<0.0005; P-selectin: −79.9%, p<0.0002; MHC II: −78.3%, p<0.0002). There were no significant differences in surface expression of MHC class I and CD31.

Similarly, embedding human aortic endothelial cells in a three-dimensional biocompatible matrix altered the expression of surface molecules. Human aortic endothelial cells grown in a 3D matrix exhibited a significantly reduced expression profile of CD58 and showed a significant lack in upregulation of costimulatory and adhesion molecules. However, there were no significant differences in ICAM-1, E-selectin, MHC I, and CD31 expression levels between human aortic endothelial cells embedded in Gelfoam and human aortic endothelial cells grown on tissue culture polystyrene plates. Furthermore, there were no significant differences in constitutive expression of PD-L2 (100%, p=0.73) and in upregulation of PD-L1 (86%, p=0.09).

Thus, embedding endothelial cells in a three-dimensional biocompatible matrix reduces costimulatory and adhesion molecules. Matrix embedded porcine aortic endothelial cells and human aortic endothelial cells exhibited significantly lower expression levels of costimulatory and adhesion molecules on activated endothelial cells.

Expression of CD31, MHC-II, CD58, ICAM-1 and E-selectin was also analyzed in the implants in vitro by confocal microscopy and in rats in vivo by immunohistochemical analysis. Endothelial cells were seeded on cover slips or embedded in Gelfoam-matrices. After washing with PBS and fixation with 3% paraformaldehyde for 20 min (cover slips) or overnight (Gelfoam), endothelial cells were blocked with rat serum (Bethyl Laboratories, TX) for 30 min. Before staining with antibodies, Gelfoam matrices were cut into 2 mm thick slices. Endothelial cells were stained with the appropriate amount of antibodies for 1 (cover slips) or 2 hours (Gelfoam) and analyzed on a Zeiss LSM510 Laser scanning confocal microscope. Staining intensity was quantified with ImageJ software (National Institute of Health, Bethesda, Md.) and normalized against CD31 expression.

Confocal microscopy revealed reduced expression-levels of CD58, ICAM-1, E-selectin, and MHC-II on matrix embedded porcine aortic endothelial cells whereas CD31 expression remained unchanged (p<0.02). Cell-substrate anchoring had no effect on MHC-I expression but markedly muted the expected upregulation of MHC-II molecules. Porcine aortic endothelial cells embedded in Gelfoam evoked only a modest proliferation of xenogeneic $CD4^+$ T cells in-vitro similar to the response seen with blockade of MHC-II binding in free porcine aortic endothelial cells.

Modulation of the Immune Response In Vivo

Matrix embedded porcine aortic endothelial cells showed a lower stimulation of the initial event in the recruitment of leukocytes which involve P- and E-selectin, and of VCAM-1 which is closely associated with T cell recruitment at sites of immune inflammation. The full panel of general and species specific costimulatory molecules was down regulated by matrix embedding, including the first report of endothelial cell-expression and suppression of 4-1BB-ligand. At the same time, expression and upregulation of PD-L1 and PD-L2, members of the B7-family that act as countervailing inhibitory molecules, remained intact after matrix embedding. These in-vitro findings translated into a significantly muted immune reaction in rats after implantation of matrix-embedded porcine aortic endothelial cells.

The cellular response to implantation was also evaluated immunohistochemically in six rats from each group on day 28 post implantation. Five-micrometer paraffin sections were cut and antigen retrieval performed by microwave heating for 10 minutes in a 0.01 mol/L citrate buffer, pH 6.0. Leukocytes, T and B lymphocytes were identified by an avidin-biotin peroxidase complex method. The primary antibodies were mouse anti-rat CD45R0, to identify leukocytes (Research Diagnostics; 1:50 dilution), mouse anti-rat CD4, to identify $CD4^+$-T cells (Pharmingen; 1:10 dilution), and mouse anti-rat CD8, to identify $CD8^+$-T cells (Pharmingen; 1:50 dilution). Rat spleen was used as a positive control, and mouse IgG as negative controls. Primary antibodies were applied for 1 hour at room temperature, and all sections were counterstained with Mayer's hematoxylin solution (Sigma). Six nonoverlapping fields (×600) were examined. The results for each group were averaged.

Embedding endothelial cells in a three-dimensional biocompatible matrix, as compared to injected free PAE or PAE injected adjacent to a three-dimensional biocompatible matrix, also reduced the immune response in rats in vivo. Porcine aortic endothelial cells embedding in Gelfoam significantly reduced formation of porcine aortic endothelial cell-specific IgG in vivo. Serum cytokines (MCP-1, IL-6, to TNF-α) rose, peaking five days after implantation, in rats receiving free porcine aortic endothelial cells and injections of porcine aortic endothelial cells adjacent to Gelfoam. In contrast, cytokine levels did not increase above background in animals with matrix-embedded porcine aortic endothelial cells.

Immunohistological studies revealed evidence of cellular infiltration into and around the implants/injection site at 28 days. After injection of free porcine aortic endothelial cells and injection of porcine aortic endothelial cells adjacent to Gelfoam, T cells were abundant within the implant/injection side, whereas large numbers of CD45R0 positive leukocytes were also found at the periphery of the graft. In contrast, the tissue surrounding the implant and Gelfoam-porcine aortic endothelial cells itself were infiltrated with 4.5 fold fewer leukocytes and $CD4^+$-T cells, and 3.3 fold fewer $CD8^+$ T cells than the other cell implantation groups.

Circulating rat immunoglobulins specific for the implanted porcine aortic endothelial cells were also measured by flow cytometry. $2 \times 10^5$ porcine aortic endothelial cells were detached from tissue culture polystyrene plates with 0.25% trypsin/0.04% EDTA, pelleted, washed, resuspended in FACS buffer and incubated with serum from recipient rats for 30 min at 4° C. (diluted 1:10 in FACS buffer). After washing twice with cold FACS buffer, cells were incubated with FITC-conjugated anti-rat IgG. Following 30 min incubation at 4° C. in the dark, the samples were again washed twice with cold FACS buffer, fixed in 1% paraformaldehyde, and $10^4$ cells were analyzed by flow cytometry using a FACScalibur instrument and CellQuest software. Rat IL-6 (R&D Systems, MN, detection limit 21 pg/ml), rat TNF-α (R&D Systems, detection limit <5 pg/ml), and rat MCP-1 (Amersham, detection limit <5 pg/ml) serum-concentrations were quantified by ELISA on days 0, 5, 12, and 28 post implantation. Measurements were performed at the same time by the same ELISA to avoid variations of assay conditions.

The levels of immunoglobulins specific for the implanted porcine aortic endothelial cells in serum of the experimental mice were also measured by flow cytometry. $2 \times 10^5$ porcine aortic endothelial cells, from the same strain as the implanted cells, were detached from cell culture plates with 0.25% trypsin/0.04% EDTA, pelleted, washed, and resuspended in FACS buffer (PBS, 1% FCS, 0.1% sodium azide). These cells were then incubated with serum from recipient mice for 60 min at 4° C. (diluted 1:10 in FACS buffer). After washing twice with FACS buffer, cells were incubated with FITC-conjugated rat anti-mouse $IgG_{2a}$ (Southern biotechnology, AL), $IgG_1$ (clone A85-1), or IgM (clone R6-60.2, BD Pharmingen, CA) respectively. Following 30 min incubation at 4° C. in the dark, the samples were again washed twice with cold FACS buffer, fixed in 0.25 ml 1% paraformaldehyde, and $10^4$ cells were analyzed by flow cytometry using a FACScalibur instrument and CellQuest software.

Figure 1B:
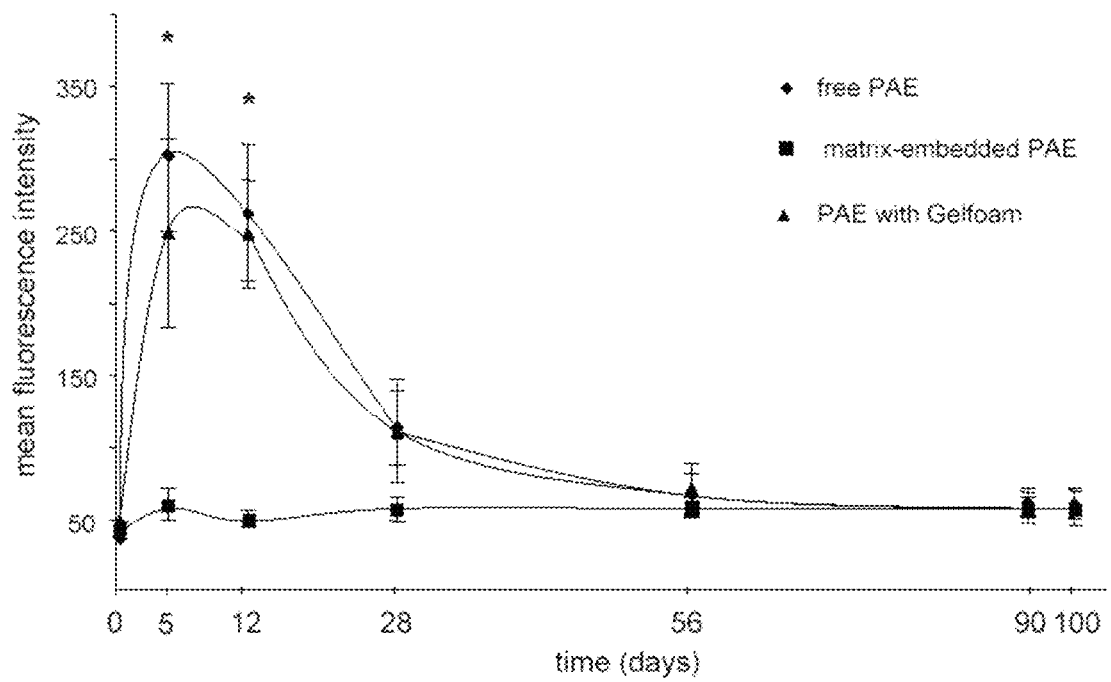

Embedded endothelial cells in a three-dimensional biocompatible matrix, as compared to injected free PAE and PAE injected adjacent to a three-dimensional biocompatible matrix, reduced the Th2-driven immune response in mice in vivo. To characterize the magnitude and nature of the porcine aortic endothelial cell-specific antibody response, serum was collected from mice after implantation of porcine aortic endothelial cells in the subcutaneous dorsal space as Gelfoam-embedded cells, saline-suspended cell pellets, or as pellets adjacent to empty Gelfoam. Post-implantation anti-porcine aortic endothelial cell $IgG_1$ and IgM levels were similar and significantly higher in mice receiving porcine aortic endothelial cell pellets or porcine aortic endothelial cell pellets adjacent to empty Gelfoam compared to recipients of porcine aortic endothelial cells embedded in Gelfoam (FIGS. 1A and 1B). There was a transient and minor elevation in anti-porcine aortic endothelial cell $IgG_{2a}$ 12 days after implantation (p<0.005) after implantation of matrix-embedded porcine aortic endothelial cell mice which was not seen in mice receiving pelleted porcine aortic endothelial cells or implants of empty Gelfoam with injection of pelleted porcine aortic endothelial cells (FIG. 1C).

Figure 1C:
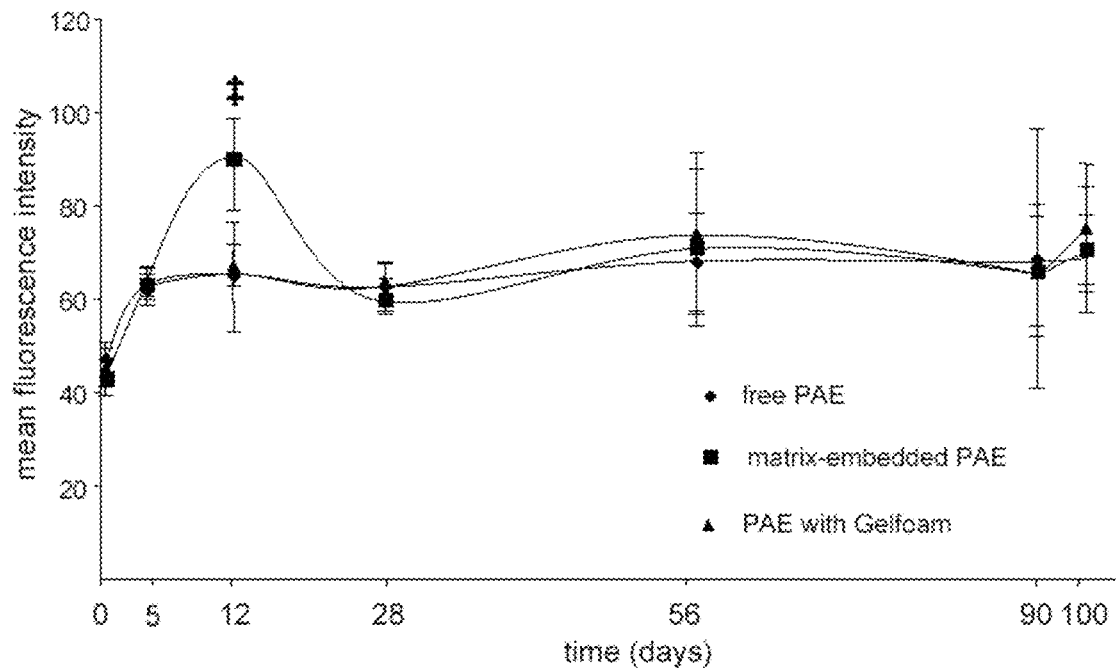

FIGS. 1A, 1B and 1C graphically depict circulating PAE-specific IgG in mice after subcutaneous injection of free PAE, of Gelfoam-grown endothelial cells, or after concomitant injection of PAE adjacent to Gelfoam alone as determined via flow-cytometry. Graphic depiction of results from all mice (n=18 per group to day 28, n=12 per group day 56-100 post-implantation) demonstrates a statistically significant difference between the matrix-embedded and other forms of PAE implantation for $IgG_1$ (FIG. 1A) and IgM (FIG. 1B). There was a transient and minor elevation in anti-PAE $IgG_{2a}$ 12 days after implantation of matrix-embedded PAE (FIG. 1C).

Compared to unstimulated HAE grown on tissue culture plates, matrix-embedded HAE expressed significantly higher levels of the inhibitory signaling molecules suppressor-of-cytokine-signaling $(SOCS)_3$ (0.007±0.001 vs. 0.003±0.0003 RU, p<0.001). Hence stimulation with IFN-γ resulted in significantly lower expression of MHC II on matrix-embedded HAE (37±5 vs. 68±4%, p<0.001). Despite unchanged IFN-γ-receptor expression levels (p=0.39) substrate adherence reduced IFN-γ-induced phosphorylation of Janus kinase 1 and 2 and signal-transducer-and-activator-of-transcription-1. This was followed by diminished expression of interferon-regulatory factor-1, CIITA (0.01±0.004 vs. 0.03±0.004 RU, p<0.005), and HLA-DR (0.17±0.04 vs. 0.27±0.05 RU, p<0.02) in matrix-embedded HAE. Reduced MHC II expression on matrix-embedded HAE resulted in muted ability to induce proliferation of allogeneic T cells (4152±255 vs. 19619±327 cpm, p<0.001).

Interestingly, embedding endothelial cells in a three dimensional matrix nearly completely diminishes the observed Th2-driven immune response, mutes lytic activity and attenuates differentiation of naïve T cells into effector cells. In accordance with previous results, these data suggest that Gelfoam embedding of cells provides immune protection by immune activation at the T-cell level via reduced expression levels of MHC class II molecules as well as costimulatory and adhesion molecules.

Modulation of Lymphocyte Proliferation and Lytic Activity.

Porcine aortic endothelial cells grown on polystyrene wells or embedded in Gelfoam were seeded in 96 well plates at $5×10^4$ cells/well and stimulated with 40 ng/ml porcine INF-γ for 48 hours, followed by mitomycin C treatment (Sigma, 50 μg/ml for 30 min) to prevent background proliferation. Human $CD4^+$ lymphocytes were purified by negative selection with a $CD4^+$ T cell isolation kit II (Miltenyi Biotec, Germany) according to the manufacturer's instructions and added at $2×10^5$ cells/well. In some experiments a murine antibody directed against HLA-DP, DQ, DR blocked activation via MHC class II molecules. $^3$[H]-thymidine incorporation was measured on day 6 by 16 h pulse (1 μCi/ml, Amersham). Thymidine uptake of mitomycin-treated porcine aortic endothelial cells, medium or T cells alone was used as negative controls.

To evaluate lymphocyte lytic activity in mice in vivo, splenocyte isolation and evaluation was performed. Spleens of 4 mice from each group were isolated aseptically in a laminar flow hood on day 28 after porcine aortic endothelial cell-implantation. Organs were cut in several pieces. Clumps were further dispersed by drawing and expelling the suspension several times through a sterile syringe with a 19-Gauge needle. Afterwards, the suspension was expelled through a 200 μm mesh nylon screen. Cells were washed twice with RPMI (containing 2 mM L-glutamine, 0.1 M HEPES, 200 U/ml Penicillin G, 200 μg/ml streptomycin and 5% heat-inactivated calf serum, Life Technologies) and immediately used.

To further evaluate lymphocyte lytic activity in mice in vivo, a Calcein-AM release assay was performed. Porcine aortic endothelial cells from the same strain of injected cells were resuspended in complete medium at a final concentration of $2×10^4$/well and incubated with 15 μM calcein-AM (Molecular Probes) for 40 min at 37° C. with occasional agitation. After two washes with complete medium, splenocytes as effector cells were added at a final concentration of $5×10^5$/well. Spontaneous and maximum release were examined as controls in six replicate wells that contained only target cells in complete medium and six wells with target cells in medium plus 2% Triton X-100 for the last 20 minutes. After 3 hour incubation at 37° C./5% $CO_2$ samples were measured using a Fluoroskan Ascent FL dual-scanning microplate luminofluorimeter (Thermo Electron Corporation, TX). Data were expressed as arbitrary fluorescent units (AFU). Specific lysis was calculated according to the formula [(test release-spontaneous release)/(maximum release-spontaneous release)]×100.

Embedding endothelial cells in a three-dimensional biocompatible matrix reduced lymphocyte proliferation. The proliferative response of isolated human $CD4^+$ T cells to untreated and INF-γ treated porcine aortic endothelial cells (40 ng/ml. 48 hours) grown in tissue culture plates or embedded in Gelfoam was assayed by thymidine incorporation. The strong $CD4^+$ T cell proliferation noted after exposure to porcine aortic endothelial cells pretreated with INF-γ was nearly eliminated when porcine aortic endothelial cells were matrix-embedded (17087.2±3749.75 vs. 5367.8±1976.3 cpm, p<0.01). The presence of MHC II antibody blocked lymphocyte proliferation in response to INF-γ-treated porcine aortic endothelial cells by 65% to a level comparable to matrix embedded porcine aortic endothelial cells. Mitomycin-treated porcine aortic endothelial cells did not show a significant proliferation after 6 day culture (61±13 cpm) as well as culture of isolated $CD4^+$ T cells alone (83±27 cpm).

Figure 2:
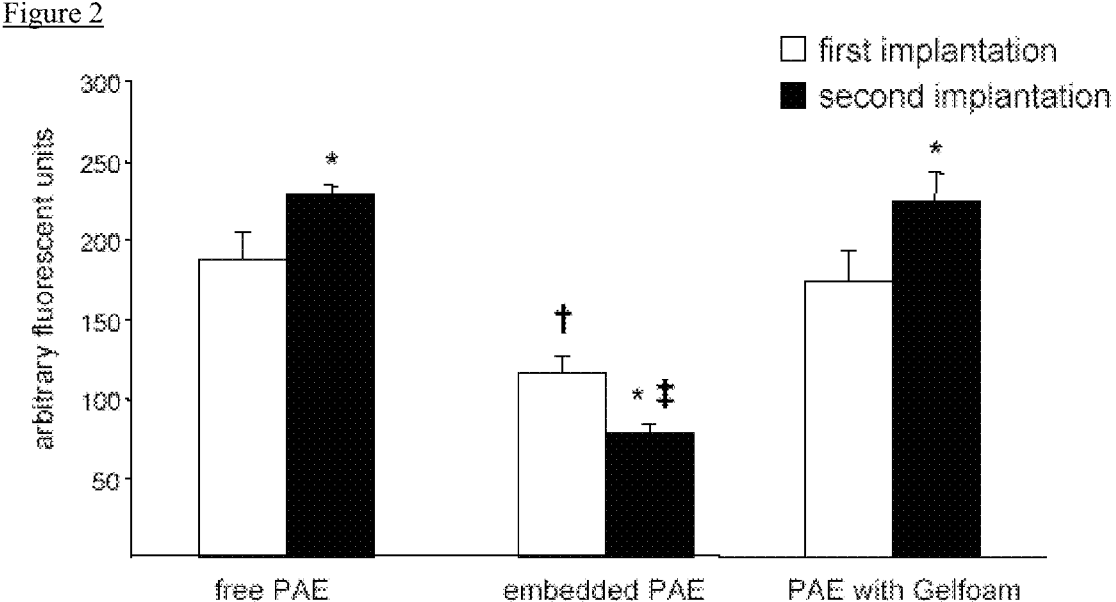
FIG. 2 graphically depicts lytic activity of splenocytes according to an illustrative embodiment of the invention.

Similarly, embedding endothelial cells in a three-dimensional biocompatible matrix, as compared to injected free PAE and PAE injected adjacent to a three-dimensional biocompatible matrix, reduced lymphocyte lytic activity in mice in vivo. Lymphocytes from mice spleens from the three different treatment groups were isolated 28 days after porcine aortic endothelial cell implantation. Donor porcine aortic endothelial cells were labeled with Calcein-AM and endothelial cell-lysis was measured by a calcein fluorescence release assay after coincubation with lymphocytes. Lymphocytes from mice after pure porcine aortic endothelial cell-injection (36.8±3.9%) and after concomitant porcine aortic endothelial cell-injection (33.9±4.7%) showed the highest lytic activity as compared to lymphocytes isolated from mice after implantation of porcine aortic endothelial cell-Gelfoam constructs (22.4±4.2%, p<0.05; FIG. 2).

FIG. 2 graphically depicts splenocytes from mice receiving free PAE and shows significantly increased lytic activity when compared to matrix-embedded PAE. Rechallenge of mice with free PAE significantly increased xenogeneic lytic activity of isolated splenocytes.

Modulation of Th2 Cytokine-Producing Cells and Cytokines.

Immunospot plates (Millipore, Bedford, Mass.) were coated with 5 μg/ml of anti-mouse interferon (IFN)-γ, anti-mouse interleukin (IL)-2, anti-mouse IL-4, or anti-mouse IL-10 mAb (all BD Pharmingen) in sterile PBS overnight. The plates were then blocked for two hours with complete RPMI-medium without phenol red, containing 10% heat-inactivated calf serum. Splenocytes ($0.5×10^6$ in 100 μl complete RPMI-medium) and the same strain of porcine aortic endothelial cells used for implantation ($0.5×10^6$ in 100 μl complete RPMI-medium) were then placed in each well and cultured for 48 hours at 37° C. in 5% $CO_2$. After washing with deionized water followed by washing with PBS containing 0.05% Tween (PBST), 2 μg/ml of biotinylated anti-mouse IFN-γ, anti-mouse IL-2, anti-mouse IL-4, or anti-mouse IL-10 mAb (all BD Pharmingen) were added overnight respectively. The plates were then washed three times in PBST, followed by one hour of incubation with horseradish peroxidase—conjugated streptavidin (BD Pharmingen). After washing four times with PBST followed by PBS, the plates were developed using 3-amino-9-ethyl-carbazole (BD Pharmingen). The resulting spots were counted on a computer-assisted enzyme-linked immunospot image analyzer (Cellular Technology Ltd., ORT). The number of spots in the wells with medium, splenocytes or porcine aortic endothelial cells alone was subtracted from xenoresponses to account for background in data analysis.

Figure 3A:
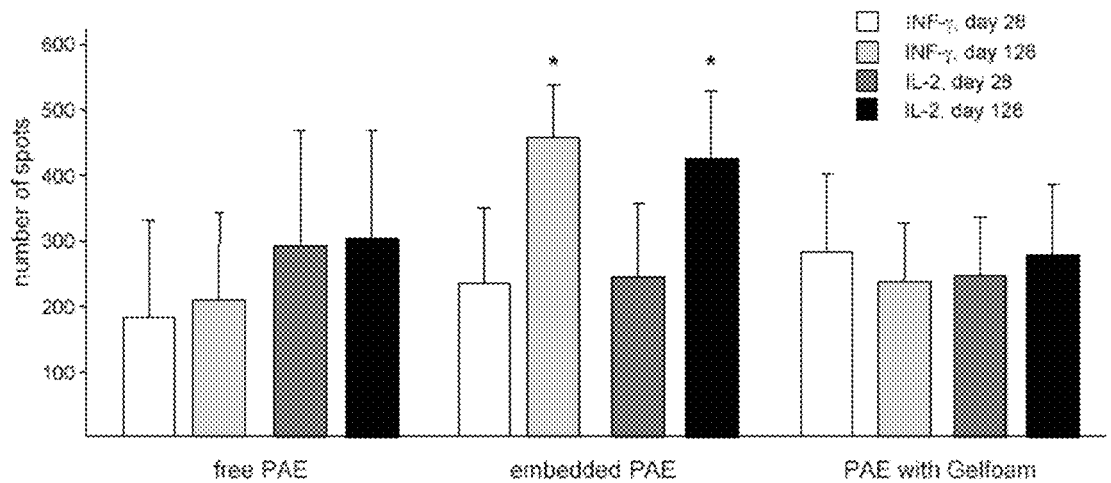
FIG. 3A graphically depicts the frequencies of cytokine-producing cells according to an illustrative embodiment of the invention.

Embedding endothelial cells in a three-dimensional biocompatible matrix, as compared to injected free PAE and PAE injected adjacent to a three-dimensional biocompatible matrix, reduced Th2 cytokine-producing cells in mice in vivo. The frequency of Th1 cytokine (IFN-γ, IL-2) and Th2 cytokine (IL-4, IL-10)-producing cells was measured by ELISPOT assay in splenocytes recovered from animals after implantation of different forms of porcine aortic endothelial cells. At day 28 postimplantation, the frequency of Th2 cytokine-producing cells was significantly lower in splenocytes isolated from mice receiving matrix embedded porcine aortic endothelial cells compared with those isolated from mice receiving free porcine aortic endothelial cells or porcine aortic endothelial cells adjacent to empty Gelfoam ((IL-4: $p<0.0001$, IL-10<0.001; FIG. 3A). In contrast, there were no significant differences in the frequency of Th1 cytokine-producing cells in splenocytes isolated from the three groups (FIG. 3B).

FIG. 3A graphically depicts the frequencies of xenoantigen-specific cytokine-producing cells in recipients after implantation of mice with free PAE, matrix-embedded PAE, or PAE injection adjacent to empty Gelfoam. There were no significant differences in frequency of xenoreactive INF-γ and IL-2 producing T-cells between the three groups on day 28. However, rechallenge with matrix-embedded PAE evokes a significant increase in xenoantigen-specific INF-γ and IL-2 producing T-cells.

Figure 3B:
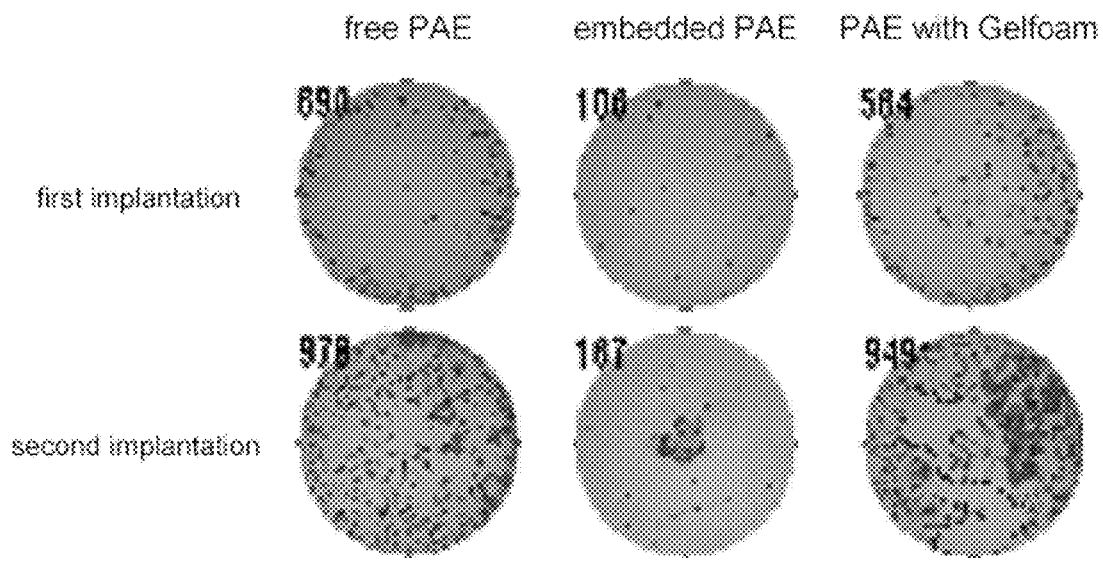
FIG. 3B depicts representative ELISPOT wells according to an illustrative embodiment of the invention.

FIG. 3B depicts representative ELISPOT wells for one mouse of each treatment group 28 days after first implantation and second implantation respectively. IL-4 production in response to PAE was measured. The number of IL-4 spots in each well was determined by computer-assisted image analysis.

Figure 3C:
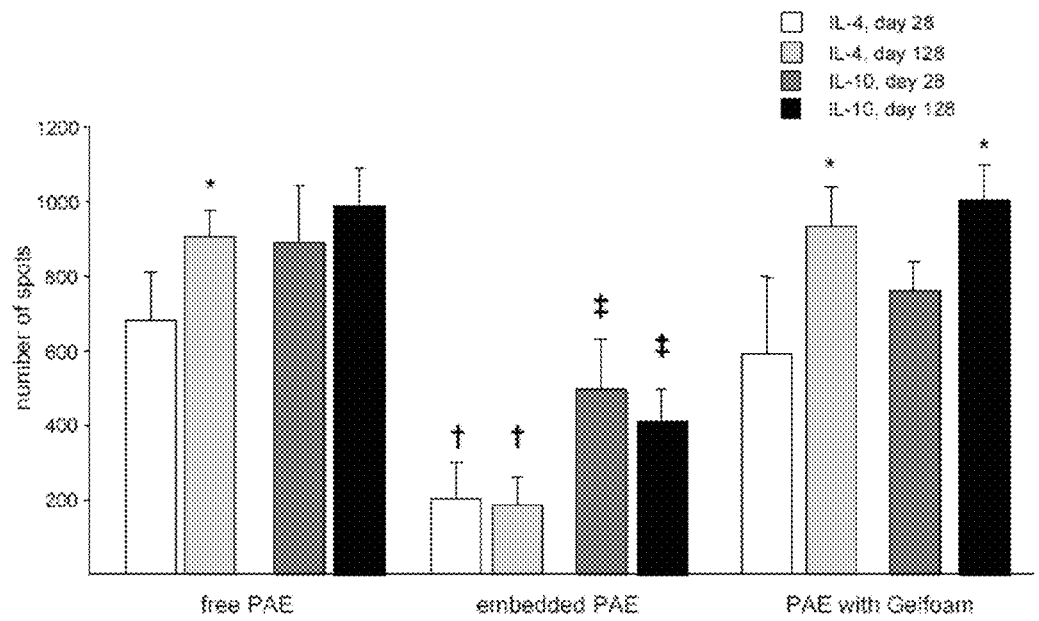
FIG. 3C graphically depicts the frequencies of T cells according to an illustrative embodiment of the invention.

FIG. 3C graphically depicts that recipients of free PAE exhibited a significant increased frequency of xenoreactive IL-4 and IL-10 producing T-cells compared to recipients of matrix-embedded PAE on day 28. Rechallenge with free PAE or PAE injection adjacent to empty Gelfoam matrices significantly increased frequency of xenoantigen-specific IL-4 and IL-10 producing T-cells on day 128.

Modulation of Effector Cells.

Splenocytes recovered from the recipients were resuspended in FACS buffer at a concentration of $2\times10^6$/ml. Cells were stained with anti-CD4 FITC (clone L3T4), antiCD8 FITC (clone Ly-2), anti-CD44 R-PE (clone Ly-24), and anti-CD62L allophycocyanin (clone Ly-22), and isotype controls (all BD PharMingen). CD4$^+$ and CD8$^+$ effector cells expressing CD44$^{high}$ and CD62L$^{low}$ were enumerated, as previously described.

Embedding endothelial cells in a three-dimensional biocompatible matrix prevented xenorejection in mice in vivo. To determine the effect of matrix embedding on the generation and function of xenoreactive CD4$^+$ and CD8$^+$ T cells, we measured the number of CD62L$^{low}$CD44$^{high}$ found in the spleens of mice treated after implantation of matrix-embedded porcine aortic endothelial cells, implantation of saline-suspended cell pellets, or as pellets adjacent to empty Gelfoam 28 days following implantation (FIG. 4). CD4$^+$ and 8$^+$ effector cells have been reliably identified as CD62L$^{low}$CD44$^{high}$ cells. The percentage of CD62L$^{low}$CD44$^{high}$ cells increased significantly in free porcine aortic endothelial cell-recipients and mice receiving porcine aortic endothelial cells adjacent to empty Gelfoam compared with mice receiving matrix-embedded porcine aortic endothelial cells; the frequency of CD4$^+$CD62L$^{low}$CD44$^{high}$ T cells outnumbered CD8$^+$ effector cells in all groups (ratio 1.7-2.3).

Figure 4A:
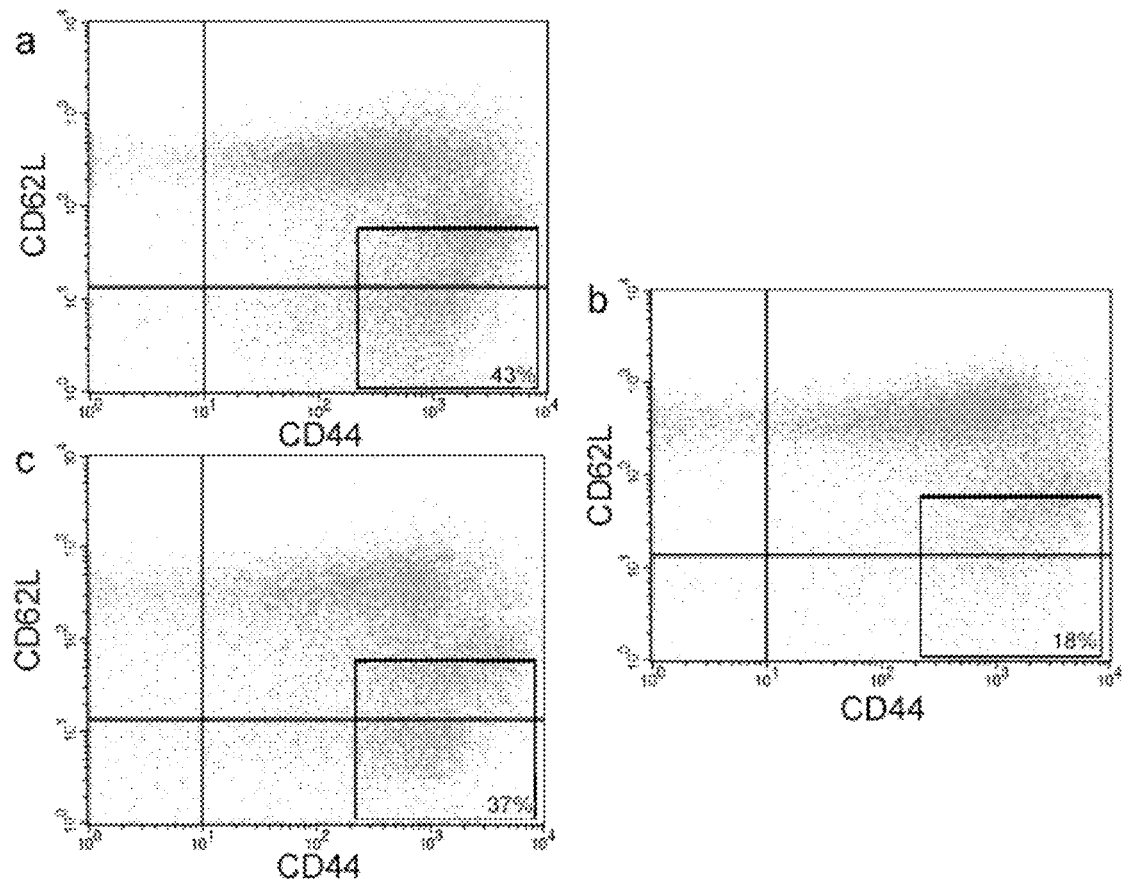
FIGS. 4A and 4B graphically plot levels of effector cells according to an illustrative embodiment of the invention.

FIG. 4A graphically plots significantly increased CD4$^+$ and CD8$^+$ effector cells in mice receiving free PAE. CD4$^+$ effector cells outnumbered CD8$^+$ T-cells on days 28 and 128. CD4$^+$ splenocytes recovered from mice were analyzed by flow cytometry using CD62L and CD44 as markers for effector T cells. Representative plots from mice receiving free (a), matrix-embedded (b), or PAE adjacent to Gelfoam (c) 28 days after implantation.

Figure 4B:
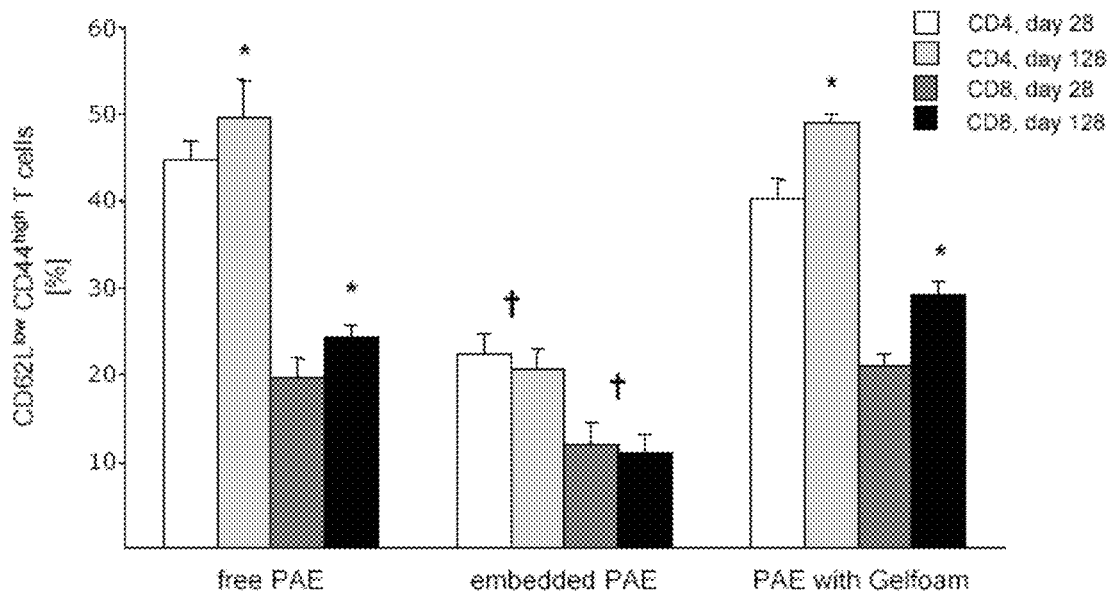

FIG. 4B graphically depicts expansion of effector cells increases after rechallenge in mice receiving free PAE but not matrix-embedded PAE.

Modulation of Xenorejection and Immunological Memory.

Embedding endothelial cells in a three-dimensional biocompatible matrix produced immunological memory after implantation of non-vascularized xenogeneic tissue. Th1 cytokines play critical roles in the prevention of xenorejection by down-regulating the Th2-driven humoral responses. In this regard, the data demonstrate that tissue engineered endothelial cells can evoke a significant increase of porcine aortic endothelial cell-specific IgG$_{2a}$ antibodies and a significant increase in xenoreactive Th1 producing splenocytes after rechallenge.

Figure 5A:
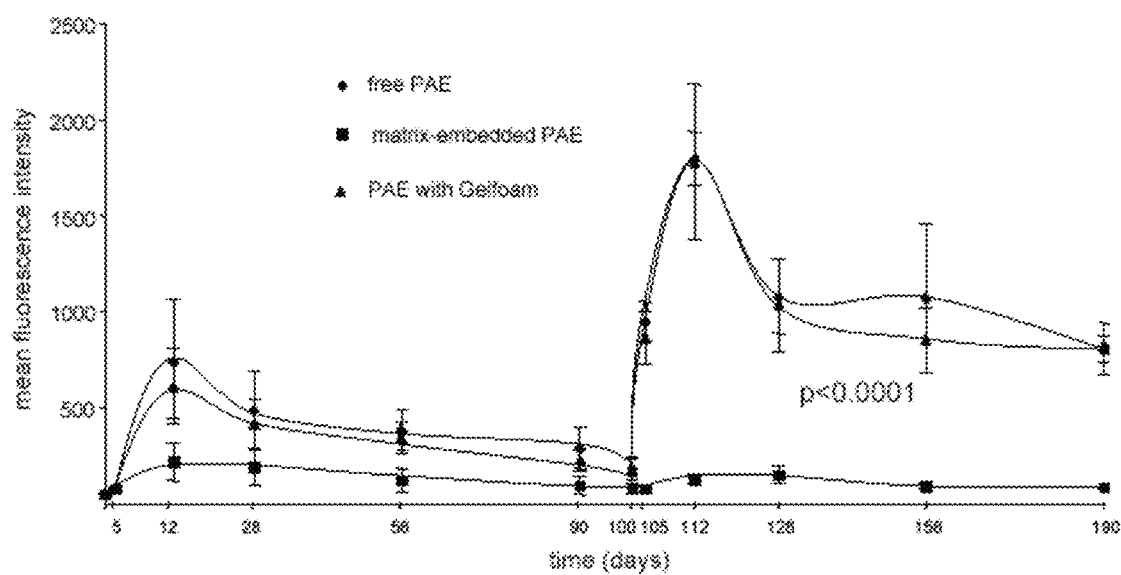
FIGS. 5A, 5B and 5C graphically depict antibody levels according to an illustrative embodiment of the invention.
Figure 5B:
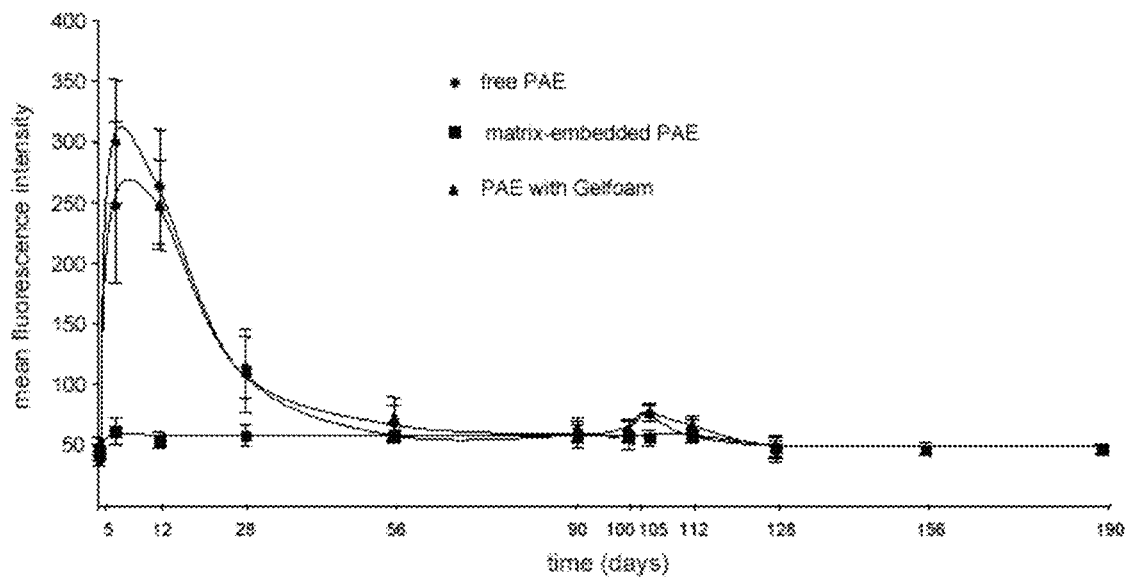

One hundred days after the first implantation, the remaining mice in each group were rechallenged with porcine aortic endothelial cells identical to their first encounter. Mice receiving saline-suspended cell pellets or pellets adjacent to empty Gelfoam showed a significant IgG$_1$-driven porcine aortic endothelial cell-specific antibody response exceeding the response observed after the first course of implantation (FIG. 5A). Only a weak IgM-antibody release was seen (FIG. 5B). In marked contrast, mice receiving matrix-embedded porcine aortic endothelial cells did not show an increase in porcine aortic endothelial cell-specific anti-IgG$_1$ and IgM levels but exhibited a significant release of porcine aortic endothelial cell-specific IgG$_{2a}$ antibodies that was absent in the other two mice groups (FIG. 5C).

Figure 5C:
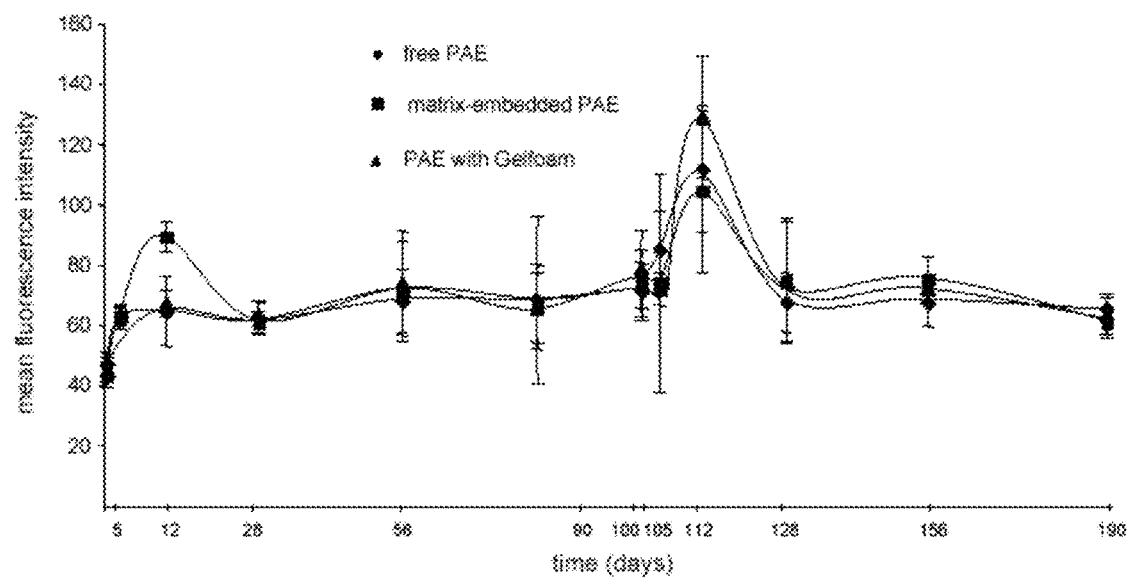

FIGS. 5A, 5B and 5C graphically depict rechallenge mice (n=12 per group to day 128, n=6 per group day 156-190 post-implantation) with free PAE or PAE adjacent to Gelfoam significantly increased formation of PAE-specific IgG$_1$-antibodies compared to rechallenge with matrix-embedded PAE (FIG. 5A). Rechallenge has no influence on PAE-specific IgM-formation (FIG. 5B) and there were no significant differences of PAE-specific IgG$_{2a}$-antibodies between the three groups (FIG. 5C).

Figure 6:
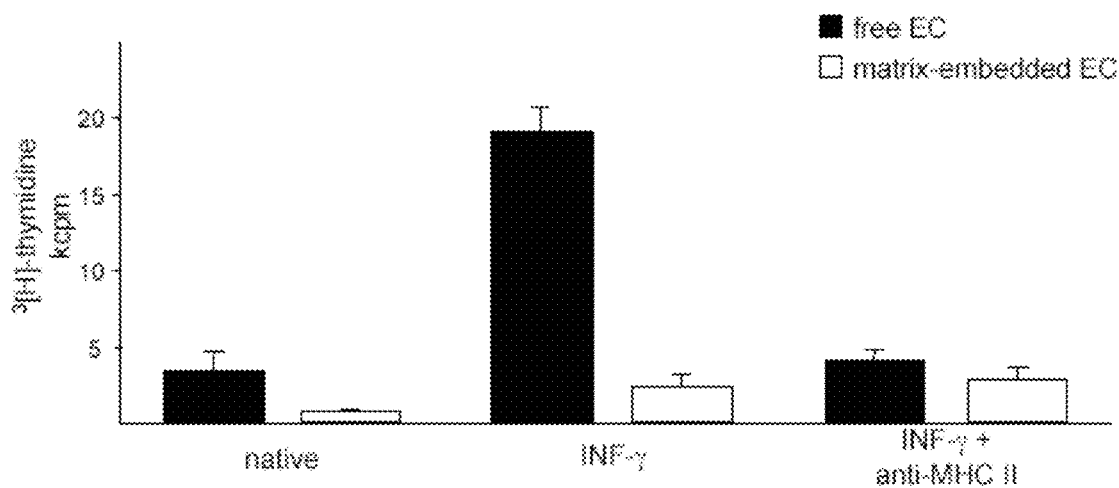
FIG. 6 graphically depicts levels of splenocytes according to an illustrative embodiment of the invention.

In line with these results, isolated splenocytes from mice receiving free porcine aortic endothelial cells or porcine aortic endothelial cell-injections adjacent empty Gelfoam showed significantly increased capability to lyse porcine aortic endothelial cells 28 days after rechallenge, whereas lysing-capability of splenocytes from mice receiving a second implant of matrix-embedded porcine aortic endothelial cells was significantly weaker than after the first implantation (FIG. 6). The frequency of xenoreactive IL-4 and IL-10 producing T cells increased significantly in mice after reimplantation of free porcine aortic endothelial cells, the frequency of Th2 producing splenocytes after rechallenge with matrix-embedded porcine aortic endothelial cells was unchanged. However, rechallenge with matrix-embedded porcine aortic endothelial cells induced a higher frequency of xenoreactive INF-γ and IL-2 producing splenocytes than after the first course of implantation.

FIG. 6 graphically depicts matrix embedding or MHC II blockade restore proliferation of mice splenocytes exposed to PAE to unstimulated levels. Mice splenocytes proliferate in response to INF-γ stimulated PAE. Matrix-embedding endothelial cells or presence of MHC II antibody blocked splenocyte proliferation in response to INF-γ treated PAE by ~79%. Each value represents mean±SD.

Furthermore, 28 days after rechallenge the percentage of $CD4^+$ effector cells further increased in mice receiving free porcine aortic endothelial cells and increased significantly in mice receiving porcine aortic endothelial cells adjacent to empty Gelfoam implants but remained unchanged in mice receiving matrix embedded porcine aortic endothelial cells. The same pattern was obvious for $CD8^+$ effector T cells.

In vitro stimulation of naïve mice splenocytes with PAE revealed a significantly muted proliferative response of splenocytes when incubated with INF-γ stimulated matrix-embedded endothelial cells compared to free endothelial cells. The presence of MHC II antibody blocked splenocyte proliferation in response to INF-γ-treated PAE by 79% to a level comparable to matrix embedded PAE.

Overall, the spleen size in mice receiving matrix-embedded porcine aortic endothelial cells appeared smaller than in the other groups at the end of the study period (62.9±9.6, 112.7±16.9, 102.5±18.8 $mm^3$; $p<0.05$).

Thus, cognate interactions between naïve T cells and resting endothelial cells can lead to tolerance in vitro and in vivo. These data document formation of immunological memory after implantation of non-vascularized xenogeneic tissue. Immunological memory was characterized by a significant increase in antigen-specific $IgG_1$ and IgM levels, lytic activity of splenocytes and tendency towards increased differentiation into effector T cells. In contrast, rechallenging mice with matrix embedding of endothelial cells led to a reduced lytic ability of splenocytes, frequency of effector $CD4^+$ and $CD8^+$ T cells was unchanged. Whereas rechallenge with matrix-embedded porcine aortic endothelial cells had no influence on generation of anti-PAE $IgG_1$ and IgM, $IgG_{2a}$ levels increased significantly.

Modulation of Fractalkine Expression.

Chemokines and adhesion molecules are critical in recruiting circulating immune cells into the vessel wall. Fractalkine has both chemoattractive and adhesive functions and is involved in the pathogenesis of atherosclerosis, cardiac allograft rejection, glomerulonephritis, and rheumatoid arthritis. We compared expression and secretion of fractalkine between free and matrix-embedded human aortic endothelial cells (HAE) via RT-PCR, Western blot, flow-cytometry and ELISA. Adhesion assays were conducted with cytokine-stimulated HAE and $^{51}Cr$ labeled natural killer (NK) cells.

HAE were stimulated with 100 U TNFα/ml (Sigma) and 100 U IFN-γ/ml (Roche) at 37° C. in a humidified air atmosphere containing 5% $CO_2$, conditions demonstrated to result in maximal fractalkine levels in cultured endothelial cells.

Flow Cytometry: Endothelial cell monolayers or endothelial cells matrix-embedded in Gelfoam were harvested after stimulation with TNFα and IFN-γ for indicated time periods. Media were aspirated and cells were washed with PBS. Monolayers were incubated in 1 mM PBS/EDTA for 5 min, and disrupted by gentle shaking. Gelfoam-grown cells were digested with collagenase type I (Worthington Biochemical, N.J.), which was shown to have no effect on CX3CL1-expression. Cell-suspensions were washed and $3\times10^5$ cells fixed in 4% paraformaldehyde for 10 min. After two washing steps, cells were resuspended in saponin-buffer (0.1% saponin, 0.05% $NaN_3$ in Hanks' Balanced Salt Solution), centrifuged and the supernatant decanted. HAE were then incubated with FITC-conjugated mouse anti-human CX3CL1 ($IgG_1$, clone 51637, R&D Systems, Minneapolis, Minn.) or a matched isotype control (clone MOPC-31C, Pharmingen) for 45 min at 4° C. Cells were then washed and $10^4$ cells were analyzed by flow cytometry using a FACScalibur instrument and CellQuest software.

Western blot analysis: Cell monolayers or cells digested from Gelfoam matrices by collagenase-treatment were washed in PBS buffer and cell lysates were prepared by incubation with lysis buffer (20 mM Tris, 150 mM NaCl, pH 7.5, 1% Triton X-100, 1% deoxycholate, 0.1% SDS and protease inhibitor; Roche). Samples were separated on 4-20% Ready Tris-HCl gels (BioRad Laboratories, Hercules, Calif.). A positive control for fractalkine detection was used, consisting of an 85- to 90-kDa form of recombinant human fractalkine lacking the carboxy-terminal 57 amino acids (R&D Systems). Proteins were then transferred onto PVDF membranes (Millipore, Billerica, Mass.) by using glycin-Tris transfer buffer. Blot membranes were blocked in Starting Block blocking buffer (Pierce, Rockford, Ill.) for 1 hour. For fractalkine-detection, blocked membranes were incubated with goat anti-human fractalkine polyclonal antibody (R&D Systems) at a dilution of 1:200 in blocking buffer overnight at 4° C. Membranes were then washed three times at room temperature with wash buffer consisting of PBS with 0.05% Tween 20 and then incubated with secondary antibody, a rabbit anti-goat IgG conjugated to horseradish peroxidase (Santa Cruz Biotechnology, Santa Cruz, Calif.) at a 1:3.000 dilution in blocking buffer for 2 hours at room temperature followed by washing in five changes of wash buffer. For detection of fractalkine bands, the blot was incubated with chemiluminescence substrate (Western Lightning Chemiluminescence Reagent Plus kit, Perkin-Elmer, Boston, Mass.) according to the manufacturer's instructions followed by exposure to X-ray film (Kodak X-Omat Blue XB-1).

ELISA: Conditioned medium from endothelial cell monolayers or endothelial cells embedded in Gelfoam after cytokine stimulation was harvested for indicated time periods. Secreted fractalkine was detected with a commercially available enzyme-linked immunosorbent assay (ELISA) detection kit (R&D Systems). Briefly 96-well Immulon plates (Fisher Scientific, Pittsburgh, Pa.) were coated overnight at room temperature with 100 µl of 4 µg/ml of mouse anti-human fractalkine capture antibody in PBS. After three washes with wash buffer (PBS-0.05% Tween-20) plates were blocked for 3 h in 1% bovine serum albumin-5% sucrose in PBS. 100 µl of standards (420 ng/ml of recombinant human fractalkine (provided with kit) was used diluted as twofold serial dilutions in diluent buffer) or conditioned medium were added, followed by incubation overnight at room temperature. After three washing steps the plate was incubated with 100 µl of 500 ng/ml mouse anti-human fractalkine detection antibody in PBS for 2 hours at room temperature followed by incubation with 100 µl of streptavidin conjugated to horseradish-peroxidase for 30 min at room temperature. Color was then developed by adding 100 µl hydrogen peroxide solution mixed with tetramethylbenzidine (R&D Systems). The optical density was then read at a wavelength of 450 nm.

NK cell-endothelial cell binding assays: HAE were grown to confluence in 6-well plates ($6\times10^5$ cell/well) or embedded in Gelfoam matrices and activated with 100 U TNFα/ml and 100 U IFN-γ/ml for 20 hours at 37° C. in a humidified air atmosphere containing 5% $CO_2$ and washed once with PBS. Gelfoam matrices were digested with collagenase type I, cells counted and plated at a concentration of $6\times10^5$ cells/well in 6-well plates for 1 hour to allow adherence. Isolated NK cells were incubated with 10 µCi of $^{51}Cr/10^6$ NK cells, washed in PBS and then resuspended (5 $10^5$/well) in 400 µl of medium alone or medium containing anti-CX3CR1 antibody at 20 µg/ml for 20 min. The NK cell suspension was added to the endothelial monolayer under gentle rocking conditions (10 cycles/min) After 30 min the medium was decanted and the wells were gently washed. Adherent cells were lysed by treating with 1% Triton in PBS. Total binding was determined by measuring individual well-associated counts per minutes using a gamma counter. The analyses illustrated were representative of at least three independent experiments.

Matrix-embedding repressed induction of fractalkine mRNA. Whereas resting endothelial cells grown on tissue culture polystyrene plates or within a three-dimensional matrix did not express fractalkine, stimulation of HAE grown on tissue culture polystyrene plates with TNFα and IFN-γ induced fractalkine mRNA expression in a time dependent manner. Fractalkine mRNA in HAE grown on tissue culture polystyrene plates expression peaked at 12 hours stimulation with cells still expressing significant amounts of mRNA after stimulation for 24 hours. In contrast, induction of fractalkine mRNA expression was significantly reduced in matrix-embedded endothelial cells at all time points studied. The maximum was also reached after 12 hours cytokine stimulation but was only ~10% of expression levels in endothelial cells grown to confluence on tissue culture polystyrene plates ($p<0.0001$).

Matrix-embedding inhibited fractalkine protein expression in HAE. Western blot analysis revealed lower protein expression levels of fractalkine in HAE embedded within Gelfoam matrices compared to endothelial cells grown on tissue culture polystyrene plates. There was no fractalkine-specific protein band detectable in unstimulated endothelial cells and in endothelial cells stimulated for 4 hours. Endothelial cells grown on tissue culture polystyrene plates expressed fractalkine after 8 hours of stimulation and exhibited maximal expression from 16 to 24 hours of stimulation with TNFα and IFN-γ. Protein-expression in matrix-embedded HAE was detectable later (12 hours), weaker and disappeared within 24 hours of cytokine stimulation.

In analogy to Western blot results, flow cytometry analysis revealed significant higher fractalkine protein expression level in HAE grown on tissue culture polystyrene plates. Whereas maximal expression on matrix-embedded endothelial cells was reached after 16 hours of cytokine stimulation (22.8±5.7%), endothelial cells grown on tissue culture polystyrene plates reached a maximal and significant increased fractalkine expression after 20 hours stimulation with TNFα and IFN-γ (76.5±8.6%; $p<0.0001$).

Experimental data indicate a reduced secretion of fractalkine from cytokine stimulated matrix-embedded endothelial cells. Fractalkine levels were also measured as cumulative levels of soluble fractalkine released into the endothelial culture supernatants by ELISA. Levels of soluble fractalkine paralleled those in Western blot and flow cytometry analysis: fractalkine secreted from HAE grown on tissue culture polystyrene plates significantly exceeded levels secreted by matrix-embedded HAE (32.2±2.4 vs. 13.8±1.7 µg/ml after 24 hours of culture; $p<0.0002$).

Experimental data indicate a reduced adhesion of NK cells to matrix-embedded endothelial cells. To study the functional relevance of our finding, an adhesion assay with $^{51}Cr$ labeled NK cell and cytokine-stimulated HAE grown on tissue culture polystyrene plates or matrix-embedded was performed next. As revealed by gamma-counting, significantly more NK-cells adhered to allogeneic HAE grown on tissue culture polystyrene plates than embedded within Gelfoam (6335±420 vs. 1735±135 cpm; $p<0.0002$; FIG. 5). The importance of fractalkine expression for NK cell adhesion to activated endothelial cells could be demonstrated as addition of 20 µg/ml anti-CX3CL1 significantly augmented adhesion of NK cells to cytokine stimulated HAE by ~74% ($p<0.005$ vs. without anti-CX3CL1). NK cells did not adhere to tissue culture polystyrene plates or Gelfoam alone.

Modulation of the Immune Response in Heightened Immune Reactivity Mice.

Endothelial cell injections induced antibody formation in mice. In naïve B6 mice three serial subcutaneous injections of $5\times10^5$ PAE raised circulating endothelial cell-specific $IgG_1$ (2210±341 vs. 53±12 mean fluorescence intensity (MFI); $p<0.0001$) and IgM antibodies compared to saline injections (136±39 vs. 49±14 MFI; $p<0.02$). There were no PAE-specific $IgG_{2a}$ antibodies detectable in serum of either mouse groups (data not shown) 42 days after first injection of PAE.

Figure 7A:
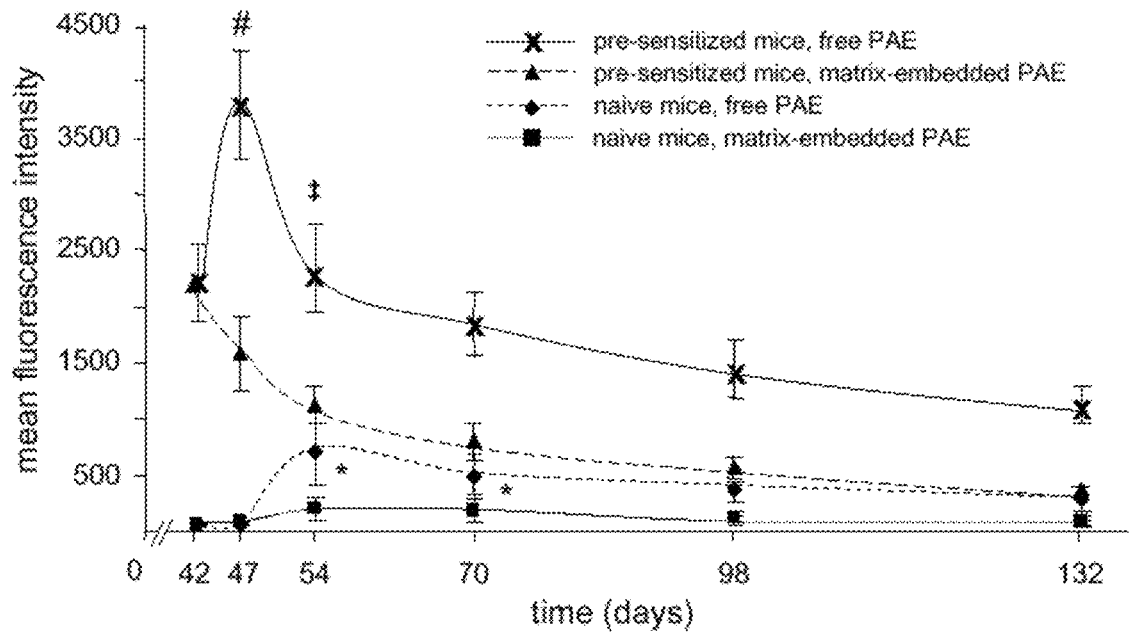
FIGS. 7A and 7B graphically depict antibody levels according to an illustrative embodiment of the invention.
Figure 7B:
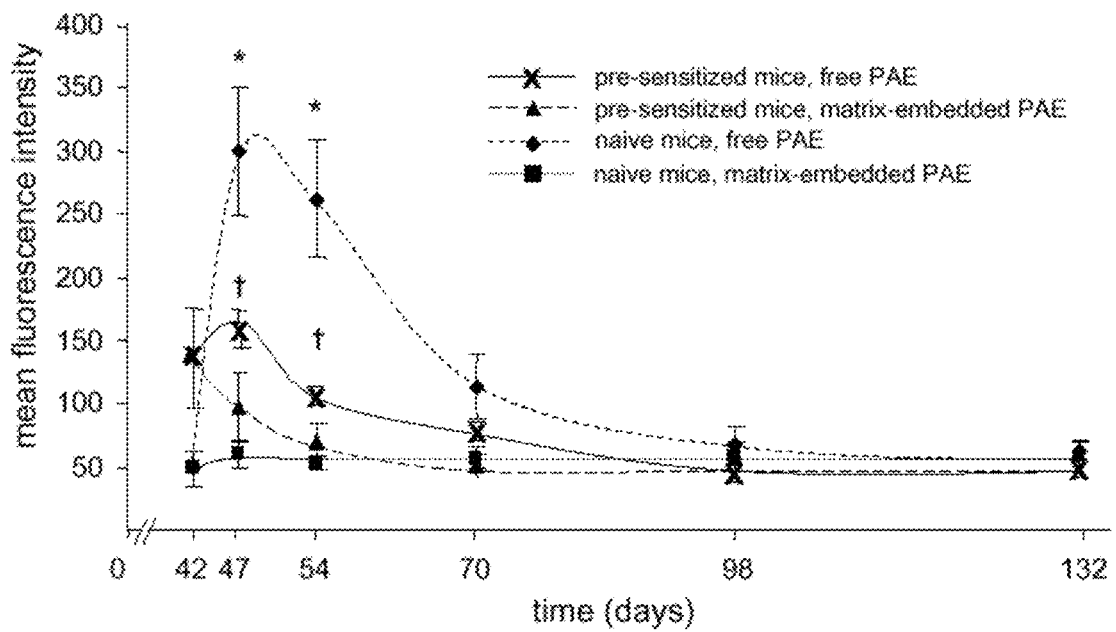

Matrix-embedded endothelial cells prevented humoral immune reactivity. Implantation of matrix-embedded xenogeneic endothelial cells, in marked contrast to implantation of free cells, failed to induce a significant humoral immune response in naïve mice (d 42, $IgG_1$: 210±102 vs. 735±327 MFI; $p<0.001$; IgM: 60±11 vs. 299±51 MFI; $p<0.001$; FIGS. 7A and 7B). Injection of free PAE in pre-sensitized serially challenged mice resulted in an elevated humoral immune response with a pronounced increase in $IgG_1$ antibody-levels (3795±448 MFI; $p<0.0002$ vs. naïve mice) and slight increase in PAE-specific IgM (164±28 MFI). In marked contrast, implantation of matrix-embedded PAE in pre-sensitized serially challenged mice did not increase PAE-specific antibodies: moreover antibody-levels specific for the injected PAE slowly decreased with time ($IgG_1$: 1578±334 MFI; $p<0.0005$ vs. free PAE; IgM: 69±5 MFI; $p<0.01$ vs. free PAE; FIGS. 7A and 7B). There was no increase in PAE-specific $IgG_{2a}$-antibodies in the four treatment groups (data not shown) supporting previous reports of a dominating Th2 response in xenografting.

FIGS. 7A and 7B graphically depict circulating PAE-specific $IgG_1$ (FIG. 7A) and IgM (FIG. 7B) in naïve and pre-sensitized serially challenged mice after subcutaneous implantation of non-embedded or matrix-embedded PAE. Graphic depiction of results from all mice (n=12/group to day 70, n=6/group day 71-132 post-implantation) demonstrates significant differences between matrix-embedded and free PAE implantation. Antibody-levels after implantation of matrix-embedded PAE slowly diminish. Data are expressed as mean values±SD.

Figure 8A:
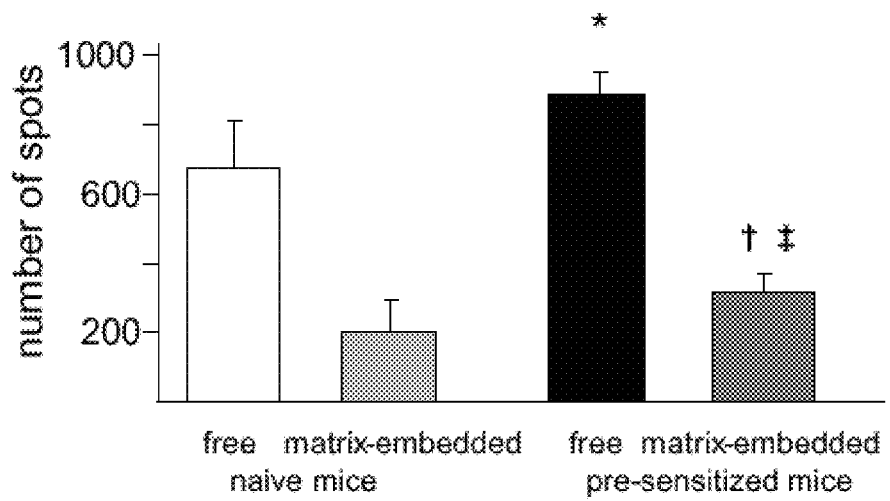
FIGS. 8A and 8B graphically depict the frequency of cytokine-producing cells according to an illustrative embodiment of the invention.
Figure 8B:
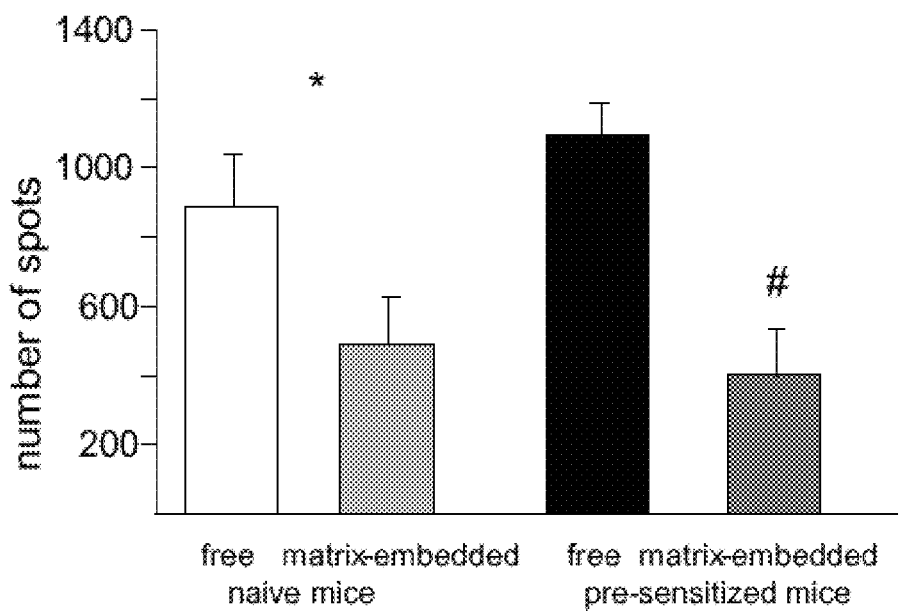

Matrix-embedded endothelial cells are poor inducers of cellular immunity. ELISPOT-analysis revealed a high frequency of xenogeneic T-helper cell (Th)2-cytokine (IL-4, IL-10) producing splenocytes in naïve and pre-sensitized serially challenged mice 90 days after implantation of free but not after implantation of matrix-embedded PAE. The frequency of xenoreactive splenocytes in pre-sensitized serially challenged mice exceeded xenoreactive splenocyte activation and differentiation in naïve mice receiving free PAE (IL-4: 907±59 vs. 680±129; $p<0.02$; IL-10: 1096±94 vs. 888±151 number of spots; $p<0.02$; FIGS. 8A and 8B). Yet, compared to implantation of matrix-embedded PAE in naïve mice, implantation of matrix-embedded PAE in pre-sensitized serially challenged mice elicited only a slight increase in IL-4 (322±75 vs. 199±99 number of spots; $p<0.05$; $p<0.0005$ vs. free PAE; FIG. 8A) but not in IL-10 producing xenoreactive splenocytes (403±142 vs. 451±135 number of spots; p=0.27; p<0.001 vs. free PAE; FIG. 8B). Significantly fewer Th2-cytokine producing splenocytes were present in pre-sensitized serially challenged mice receiving matrix-embedded PAE compared to naïve mice receiving free PAE (p<0.001). The frequency of Th1-cytokine (IFN-γ and IL-2) producing splenocytes did not differ significantly between the four treatment groups again supporting a predominant Th2-role in xenoreactivity (data not shown).

FIGS. 8A and 8B graphically depict the frequencies of xenoreactive cytokine-producing cells in recipients after implantation of free PAE or matrix-embedded PAE in naïve and pre-sensitized serially challenged mice. Data are expressed as mean values±SD. Naïve and pre-sensitized serially challenged recipients of free PAE exhibited significant increased frequencies of IL-4 (FIG. 8A) and IL-10 (FIG. 8B) producing splenocytes compared to recipients of matrix-embedded PAE.

Figure 9A:
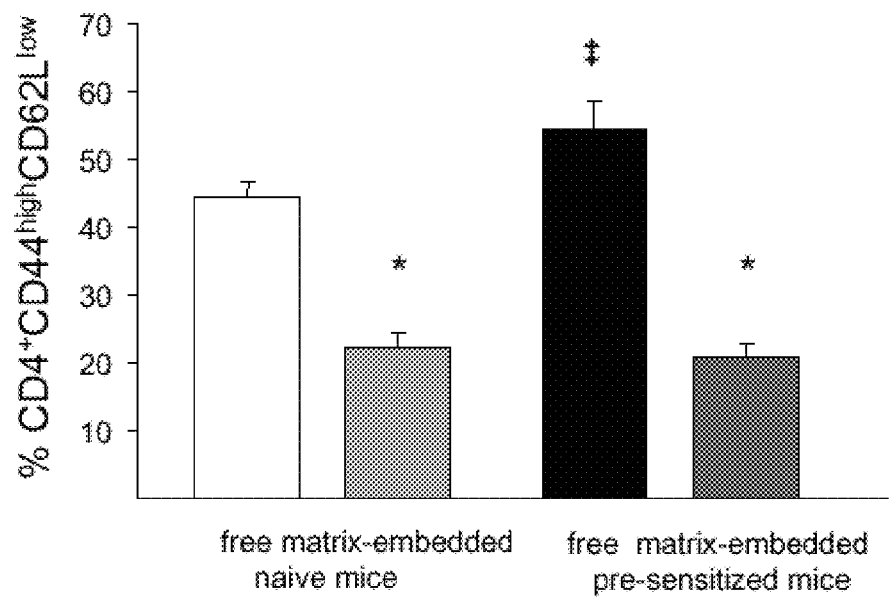
FIGS. 9A and 9B graphically depict effector cell levels according to an illustrative embodiment of the invention.
Figure 9B:
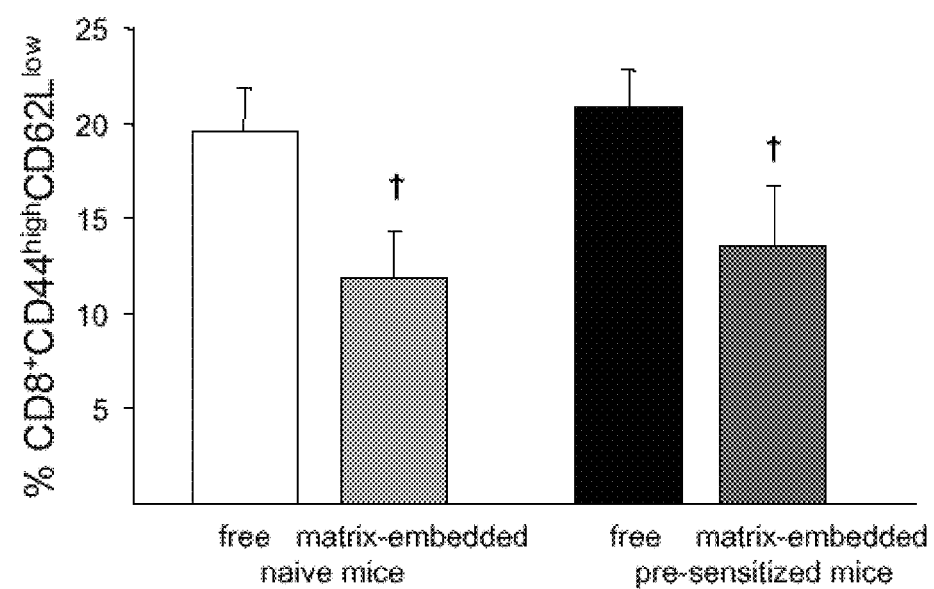

The increase in cytokine-producing splenocytes in mice receiving non-embedded PAE was paralleled by an increase of $CD4^+$ and $CD8^+$ effector T cells over time ($CD4^+$: 44±2 naïve mice, 54±4% pre-sensitized mice, p<0.05; $CD8^+$: 20±2; 21±2%; FIGS. 9A and 9B). Accordingly, differentiation of T cells into $CD44^{high}/CD62L^{low}$ T cells was significantly muted in naïve and pre-sensitized serially challenged mice exposed to matrix-embedded PAE ($CD4^+$: 22±2 naïve mice, 21±3% pre-sensitized mice; p<0.01 vs. free PAE; $CD8^+$: 12±2; 14±3%; p<0.02 vs. free PAE; FIGS. 9A and 9B). $CD4^+$ outnumbered $CD8^+$ effector T cells 1.7-2.6 in all treatment groups. A strong correlation was noted between the frequency of Th2-cytokine producing splenocytes and extent of T cell differentiation cells into $CD4^+CD44^{high}/CD62L^{low}$ (IL-4: r=0.81; p<0.0001; IL-10 r=0.88; p<0.0001; FIG. 10) and $CD8^+CD44^{high}/CD62L^{low}$ effector cells (IL-4: r=0.79; p<0.0001; IL-10 r=0.86; p<0.0001) across all treatment groups on day 132.

FIGS. 9A and 9B graphically depict significantly increased $CD4^+$ (FIG. 9A) and $CD8^+$ (FIG. 9B) effector cells in mice receiving free PAE. Splenocytes recovered from mice were analyzed by flow-cytometry using CD62L and CD44 as markers for effector T cells. No difference between naïve and pre-sensitized serially challenged mice when endothelial cells are matrix-embedded. Data are expressed as mean values±SD.

Figure 10A:
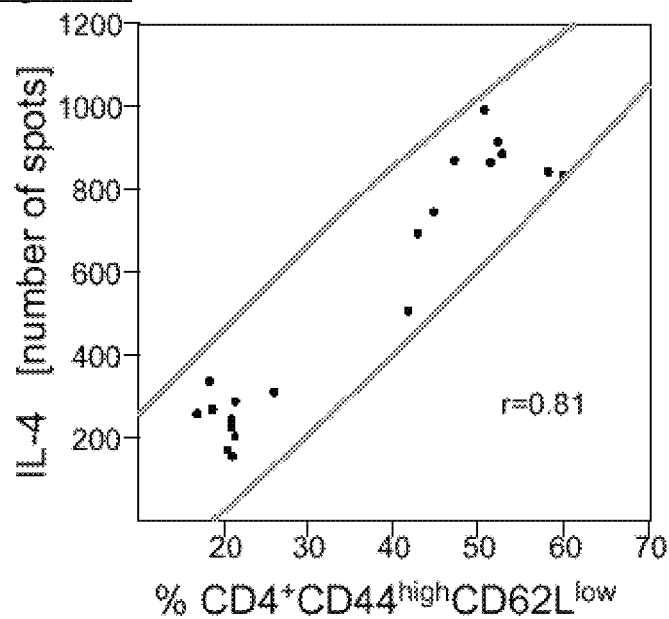
FIGS. 10A and 10B depict correlations between the frequency of Th2-cytokine producing splenocytes and the extent of T cell differentiation into effector cells according to an illustrative embodiment of the invention.
Figure 10B:
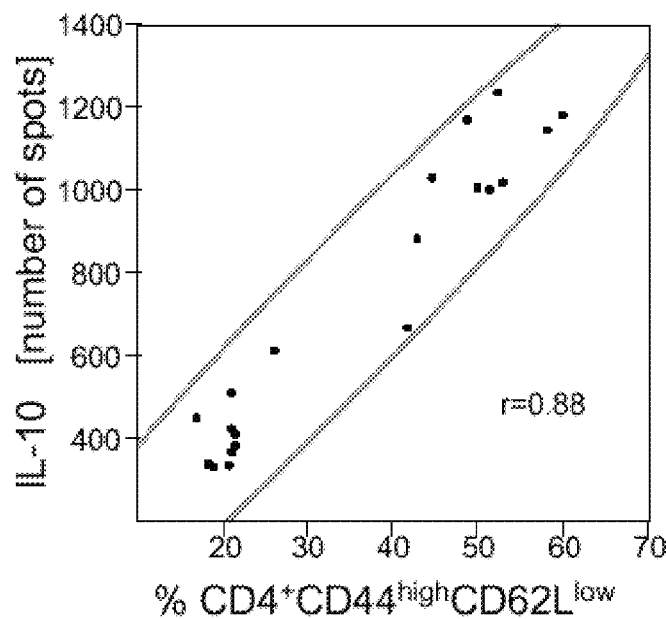

FIGS. 10A and 10B are Spearman correlations of the frequencies of Th2-cytokine producing splenocytes and the extent of T cell differentiation into effector cells. FIG. 10A graphically depicts the frequency of IL-2 cytokines. FIG. 10B graphically depicts the frequency of IL-10 cytokines. The correlations suggest that cytokine levels correlate linearly with effector T cell induction. Area of the density ellipse represents the 95% confidence interval.

Figure 11:
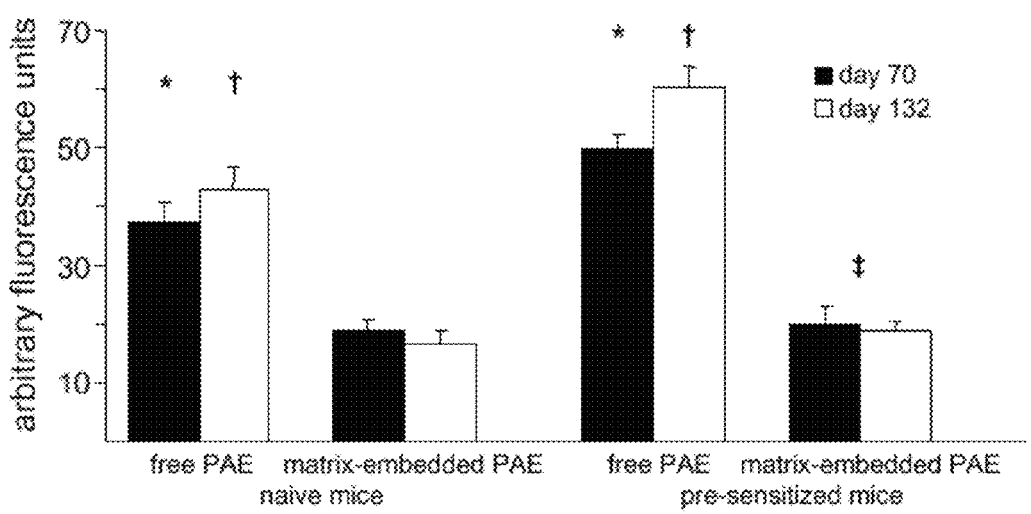
FIG. 11 graphically depicts the degree of damage to endothelial cells according to an illustrative embodiment of the invention.

Matrix-embedded endothelial cells are shielded from lytic damage. The ability of host lymphocytes to damage xenogeneic endothelial cells was characterized on day 70 and day 132. Calcein release plateaued at effector:target ratios of 25:1. For this ratio, endothelial cell damage was 1.6 fold higher in naïve mice and 1.7 fold higher in pre-sensitized mice when receiving non-embedded in place of matrix-embedded PAE on d70 (p<0.001). These ratios increased to 1.9 and 2.3 respectively after 132 days (p<0.0005; FIG. 11). Of note, the extent of endothelial damage in pre-sensitized mice receiving matrix-embedded PAE was significant lower when compared to naïve mice receiving free PAE (20.9±2.3 vs. 37.1±3 0.4% AFU; p<0.001; FIG. 11).

The ability of host lymphocytes to damage xenogeneic endothelial cells was characterized on day 70 and day 132.

FIG. 11 graphically depicts the degree of damage to endothelial cells in naïve and pre-sensitized mice when the endothelial cells are free or matrix embedded. Endothelial damage via lysis is significantly reduced in naïve and pre-sensitized mice receiving matrix-embedded compared to free PAE. $2 \times 10^4$ PAE were labeled with calcein and incubated with $5 \times 10^5$ splenocytes isolated after 70 and 132 days respectively.

Calcein release plateaued at effector:target ratios of 25:1. For this ratio, endothelial cell damage was 1.6 fold higher in naïve mice and 1.7 fold higher in pre-sensitized mice when receiving non-embedded in place of matrix-embedded PAE on day 70 (p<0.001). These ratios increased to 1.9 and 2.3 respectively after 132 days (p<0.0005; FIG. 11). Of note, the extent of endothelial damage in pre-sensitized mice receiving matrix-embedded PAE was significant lower when compared to naïve mice receiving free PAE (20.9±2.3 vs. 37.1±3.4% AFU; p<0.001; FIG. 11).

Modulation of Dendritic Cell Maturation.

Dendritic cells are antigen-presented cells that have the unique ability to both initiate and regulate immune responses. Mature dendritic cells promote T cell differentiation into effector and memory cells whereas immature dendritic cells present (self-)antigens in a tolerogenic fashion. Dendritic cells are implicated in a variety of endothelial-mediated diseases, and activated endothelial cells induce their maturation. Because dendritic cells are critical in immune reactivity, it follows that endothelial cell-driven dendritic cell maturation is dependent on endothelial cell-matrix contact.

Preparation, culture and maturation of dendritic cells: Peripheral blood was collected from healthy volunteers and fractionated over Ficoll-Paque (Sigma Chemicals, St. Louis, Mo.) by a standard procedure. To derive dendriti cells, total peripheral blood monocytic cells (PBMC) were cultured at $2 \times 10^6$ cells/ml in complete media (RPMI 1640, 10% heat-inactivated calf serum, 0.1 mM sodium pyruvate (Life Technologies)) for 1.5 hours in tissue culture flasks. Following incubation, nonadherent cells were removed by extensive washing with a 1× solution of HBSS (Life Technologies). The remaining adherent cells were then cultured in complete media containing 20 ng/ml interleukin (IL)-4 and 20 ng/ml GM-CSF (Peprotech, Rocky Hill, N.J.) for 5 days in a $CO_2$ incubator at 37° C. The resulting cells were semi- to nonadherent and MHC $II^{low}/CD14^{-/low}/CD83^-$ (data not shown).

For further maturation, adherent and nonadherent dendritic cells were harvested, extensively washed, counted and $5 \times 10^5$ dendritic cells were stimulated with a cytokine cocktail (10 ng/ml IL-1β, 1000 U/ml IL-6, 20 ng/ml IL-4, GM-CSF, and TNF-α; all Peprotech), $1.5 \times 10^5$ HAE or $1.5 \times 10^5$ PAE for 48 hours. Endothelial cells were either presented as suspensions after grown to confluence on tissue culture plates or surface adherent embedded within Gelfoam matrices. Every assay was repeated at least four times. After maturation, dendritic cells were isolated from any contaminating endothelial cells with magnetic bead-labeled CD1a antibodies (Miltenyi, Bergisch-Gladbach, Germany). Flow cytometry analysis revealed 98% purity of the isolated DC (data not shown).

Real-time PCR: Total RNA was extracted from isolated dendritic cells and the remaining endothelial cells using the RNeasy Mini Kit (Qiagen, Valencia, Calif.) according to the manufacturer's instructions. Complementary DNA was synthesized using TaqMan reverse transcription reagents from Applied Biosystems (Foster City, Calif.). Real-time PCR analysis was performed with an Opticon Real Time PCR Machine (MJ Research, Waltham, Mass.) using SYBR Green PCR Master Mix (Applied Biosystems) and selected primers. Data from the reaction were collected and analyzed by the complementary Opticon computer software. Relative quantification of gene expression were calculated with standard curves and normalized to GAPDH.

Flow cytometry: Dendritic cell or endothelial cell suspensions were washed and 3×10$^5$ cells were resuspended in FACS buffer (PBS containing 0.1% BSA and 0.1% sodium azide; Sigma Chemicals). Standard flow cytometric analysis assessed surface expression of various markers. The following monoclonal antibodies directly conjugated with phycoerythrin (PE) or fluorescein isothiocyanate (FITC) were used in single-color flow cytometric analysis: PE-CD1a (clone HI149, IgG$_1$), FITC-CD3 (clone UCHT1, IgG$_1$), PE-CD14 (clone TÜK4, IgG$_{2a}$), PE-CD31 (clone WM59, IgG$_1$), FITC-CD40 (clone 5C3, IgG$_1$), FITC-CD54 (clone 15.2, IgG$_1$), FITC-CD80 (clone BB1, IgM), FITC-CD83 (clone HB15e, IgG$_1$), FITC-CD86 (clone 2331, IgG$_1$), FITC-CD106 (clone 51-10C9, IgG$_1$), FITC-HLA-DP,DQ,DR (clone CR3/43, IgG$_1$), FITC-Toll-like receptor (TLR)2 (clone TL2.3, IgG$_{2a}$), and FITC-TLR4 (clone HTA125, IgG$_{2a}$). Appropriate isotype control antibodies (mouse PE-IgG$_1$, PE-IgG2a, FITC-IgG$_1$, FITC-IgG$_{2a}$, FITC-IgM) were used respectively. Antibodies were purchased from DakoCytomation (Carpinteria, Calif.), Serotec (Raleigh, N.C.) or PharMingen (San Diego, Calif.). After staining, cells were washed and fixed in 1% paraformaldehyde before analysis on a FACScalibur instrument and CellQuest software (Becton Dickinson, Mountain View, Calif.).

Endocytic activity: Endocytic activity of dendritic cells was measured by uptake of FITC-conjugated dextran (MW 40.000; Molecular Probes, Eugene, Oreg.) as previously described. Briefly, dendritic cells at various states of maturation were incubated in complete media with 1 mg/ml FITC-conjugated dextran for 1 hour at 37° C. to measure specific uptake, or at 4° C. to measure nonspecific binding. Cells were then washed extensively and analyzed by flow cytometry as described above.

Mixed lymphocyte reaction assay: CD3$^+$ T-cells from an unrelated donor were prepared from total PBMC by negative selection using antibody depletion and magnetic beads according to the manufacturer's instruction (Dynal Biotech, Lake Success, N.Y.). The nonmagnetic fraction contained greater than 95% CD3$^+$ T-cells, as assessed by flow cytometry. 2×10$^5$ CD3$^+$ T-cells/well were seeded in 96-well round-bottom plates. Purified cytokine- or endothelial cell-matured dendritic cells were γ-irradiated (3000 rad from a $^{137}$Cs source) and added to T-cells at 1×10$^4$, 4×10$^3$, or 2×10$^3$ cells/well to give final ratios of 1:20, 1:50, or 1:100 DC:T-cells. On day 5, 1 µCi of $^3$H-thymidine (Perkin-Elmer, Boston, Mass.) was added to each well. Cells were harvested 18 hours later and $^3$H-thymidine uptake quantified using a Packard Top-Count γ-counter (GMI, Ramsey Mich.).

Western Blot: After separation from dendritic cells, endothelial cells were washed in PBS buffer and cell lysates were prepared by incubation with lysis buffer (20 mM Tris, 150 mM NaCl, pH 7.5, 1% Triton X-100, 1% deoxycholate, 0.1% SDS and protease inhibitor; Roche, Indianapolis, Ind.). Samples were separated on 4-20% Ready Tris-HCl gels (Bio-Rad Laboratories, Hercules, Calif.). Proteins were then transferred onto PVDF membranes (Millipore, Billerica, Mass.) using glycin-Tris transfer buffer. Jurkat (TLR2) or HL-60 whole cell lysates (TLR4, both Santa Cruz Biotechnologies, Santa Cruz, Calif.) served as controls. Membranes were blocked in Starting Block blocking buffer (Pierce, Rockford, Ill.) for 1 hour. Blocked membranes were incubated with rabbit anti-human TLR2 (dilution 1:250 in blocking buffer) or TLR4 antibodies (dilution 1:200, both Santa Cruz Biotechnologies) overnight at 4° C. Membranes were then washed three times at room temperature with wash buffer consisting of PBS with 0.05% Tween 20 and then incubated with secondary antibody, a goat anti-rabbit IgG conjugated to horseradish peroxidase (Santa Cruz Biotechnology, Santa Cruz, Calif.) at a 1:1.000 dilution in blocking buffer for 2 hours at room temperature followed by washing in five changes of wash buffer. For detection of TLR bands, the blot was incubated with chemiluminescence substrate (Western Lightning Chemiluminescence Reagent Plus kit; Perkin-Elmer) according to the manufacturer's instructions followed by exposure and analysis on a Fluor Chem SP (Alpha Innotech, San Leandro, Calif.).

Non-adherent endothelial cells directed maturation of monocyte-derived dendritic cells. In line with previous observations, monocytes differentiated into immature dendritic cells after 5 days of culture in GM-CSF and IL-4 (data not shown). Prolonged cytokine-stimulation with IL-1β, TNF-α, and IL-6 for 48 hours upregulated costimulatory (CD40: 2.3 fold compared to immature dendritic cells, CD80: 1.9 fold, CD86: 1.6 fold) and HLA-DR molecules (1.5 fold) together with expression of CD83 (2.2 fold) as an established dendritic cells-maturation marker. Exposure to saline suspensions of allo- and xenogeneic endothelial cells after growth to confluence in tissue culture plates induced full maturation of monocyte-derived dendritic cells to a similar degree as prolonged treatment with a cytokine cocktail. HAE or PAE alone induced dendritic cell costimulatory molecule expression with increases in CD40 (HAE: 2.1 fold, PAE: 2.5 fold compared to immature dendritic cells), CD80 (2.1 fold, 2.3 fold; p<0.05 vs. cytokine-stimulation), CD86 (1.6 fold, 1.7), HLA-DR (1.7 fold, 2.2 fold; p<0.05 vs. HAE, p<0.002 vs. cytokine-stimulation), and CD83 (2.6 fold; p<0.05 vs. cytokine stimulation, 3.2 fold; p<0.02 vs. HAE, p<0.001 vs. cytokine-stimulation).

In a similar fashion, dendritic cell TLR2 and 4 expression were upregulated upon exposure to saline suspensions of HAE (1.5 and 2.5 fold respectively) to a similar or greater extent than cytokine stimulation (1.5 fold for both TLR compared to immature dendritic cells). This effect was even more pronounced after co-incubation of dendritic cells with non-adherent xenogeneic PAE (TLR2: 2.4 fold; p<0.05 vs. cytokine- and HAE-stimulated, TLR4: 3.0 fold; p<0.05 vs. HAE, p<0.001 vs. cytokine-stimulation). Similar results could be obtained for mRNA transcript levels. Additionally, dendritic cells matured with cytokines or non-adherent endothelial cells displayed significant upregulation of IL12 p40 mRNA (immature: 0.03±0.02 relative units (RU), cytokine-stimulated: 0.23±0.03 RU, p<0.002, HAE-stimulated: 0.31±0.05 RU, p<0.001, PAE-stimulated: 0.28±0.03, p<0.002).

Incubation with substrate-adherent endothelial cells resulted in incomplete dendritic cell-maturation and sustains endocytic activity. In marked contrast to co-culture with non-adherent endothelial cells, co-culture of dendritic cells with substrate-adherent HAE and PAE embedded within a three-dimensional matrix restricted dendritic cell maturation: these dendritic cells displayed only weak upregulation of CD40 (substrate-adherent HAE: 1.5 fold compared to immature DC, p<0.02 vs. non-adherent HAE, substrate-adherent PAE: 1.3 fold, p<0.002 vs. non-adherent PAE), CD80 (substrate-adherent HAE and PAE: 1.3 fold, p<0.005 vs. non-adherent EC), CD86 (substrate-adherent HAE: 1.1 fold, PAE: 1.2 fold, both p<0.005 vs. non-adherent EC), CD83 (substrate-adherent HAE: 1.5 fold, p<0.001 vs. non-adherent HAE, PAE: 1.4 fold, p<0.0002 vs. non-adherent PAE), and TLR4 (substrate-adherent HAE: 1.5 fold, PAE: 1.3 fold, both p<0.005 vs. non-adherent endothelial cells). Co-incubation with substrate-adherent endothelial cells failed to induce HLA-DR and TLR2 expression on dendritic cells at all (p<0.005).

Incubation with empty Gelfoam matrices alone had no effect on maturation of monocyte-derived dendritic cells (data not shown). Real-time PCR analysis revealed the same pattern of incomplete maturation when dendritic cells were exposed to substrate-adherent allo- and xenogeneic endothelial cells. Induction of IL12 p40 was similarly significantly weaker when dendritic cells had been matured with substrate-adherent endothelial cells (HAE-stimulated: 0.06±0.01, p<0.005, PAE-stimulated 0.07±0.02, p<0.02).

Immature dendritic cells efficiently captured antigen and exhibited a high level of endocytosis. FITC-conjugated dextran uptake increased when monocytes were cultured for 3 and 5 days in GM-CSF and IL-4 (423.3±121.8 mean fluorescence intensity (MFI), 239.8±42.8 MFI, p<0.0001). Maturation is typically accompanied by concomitant increase in antigen presenting function and reduced capacity for antigen capture via endocytic activity. Dextran uptake typically decreases with continued cytokine-stimulation (89.7±14.7 MFI, p<0.0001 vs. d5) and with co-incubation with non-adherent HAE (92±20.3 MFI) or PAE (82.4±16.5 MFI). In marked contrast, dendritic cells retained their endocytic activity when endothelial cells were presented in a substrate-adherent three-dimensional state and dextran uptake was markedly increased (substrate-adherent HAE: 203.2±11.3 MFI, p<0.05 vs. d5, p<0.0001 vs. non-adherent HAE; substrate-adherent PAE: 254.3±32 MFI, p<0.0001 vs. non-adherent PAE).

Dendritic cells exhibited reduced T-cell proliferation activity after cultivation with substrate-adherent endothelial cells. The ability to promote T cell differentiation into effector and memory cells is an important functional marker for the maturation grade of dendritic cells. Whereas cytokine-treated and non-adherent endothelial cell exposed dendritic cells induced T-cell proliferation over the full spectrum of dendritic cell:T-cell ratios tested (74789±1777, HAE: 97522±1630, and PAE: 101616±4302 cpm) this ability was significantly muted in dendritic cells co-incubated with substrate-adherent HAE (18320±1000 cpm, p<0.002) and PAE (20080±683 cpm, p<0.0001).

Activation of substrate-adherent endothelial cells was reduced when co-cultured with dendritic cells. Real-time PC, flow-cytometry and Western blot analysis revealed reduced activation of HAE and PAE after co-culture for 2 days with dendritic cells. After magnetic-bead based isolation of dendritic cells, the remaining cells were greater than 95% pure for the endothelial-cell specific marker CD31 (data not shown). Real-time PCR analysis demonstrated reduced mRNA expression levels for adhesion molecules, CD58, HLA-DR and TLR-molecules on substrate-adherent HAE when compared to their non-adherent counterparts. Reduced mRNA-expression levels translated into reduced surface and intracellular expression with 3.6 fold lower expression of ICAM-1 on substrate-adherent when compared to non-adherent HAE (1.3 fold decrease for PAE), 4.9 fold decrease of VCAM-1 for HAE (PAE: 2.7 fold), and 16 fold decrease of HLA-DR for HAE (PAE: 23 fold decrease). Densitometry analysis of Western blots revealed increased TLR2 (HAE: 1.5 fold increase, PAE: 1.6 fold increase; p<0.05) and TLR4 expression (HAE: 2.3 fold increase, PAE: 2 fold increase; p<0.01) in non-adherent endothelial cells when compared to substrate-adherent endothelial cells after co-incubation with dendritic cells for 48 hours.

Thus, whereas non-adherent endothelial cells induced maturation of monocyte-derived dendritic cells to an extent similar to that seen with a cytokine-cocktail, co-incubation with substrate-adherent endothelial cells induced only minor upregulation of mRNA transcript and protein levels of adhesion, costimulatory and HLA-DR molecules on dendritic cells. Dendritic cells co-incubated with substrate-adherent endothelial cells also lacked upregulation of IL12 mRNA and CD83 expression that serve as direct maturation markers. The immature state of dendritic cells after co-cultivation with substrate-adherent endothelial cells was mirrored by sustained ability to uptake dextran. Functionally, whereas dendritic cells exposed to non-adherent endothelial cells displayed enhanced T-cell stimulatory activity in mixed lymphocyte reactions, T-cell proliferation after exposure to substrate-adherent endothelial cell-matured dendritic cells was significantly weaker.

Further Experiments

Effects on Immune Response

Treatment of Transplantation Rejection:

A population of normal (not immune compromised) organ transplant recipients will be identified. The population will be divided into three groups, one of which will receive an effective amount of the implantable material of the present invention prior to receipt of a transplant organ. A second group will receive an effective amount of implantable material of the present invention coincident with receipt of a transplant organ. A third group will not receive the implantable material of the present invention, but will receive a transplant organ. Reduction of and/or amelioration of an immune response and/or an inflammatory response will be monitored over time by evaluating the proliferation of T-cell lymphocytes and B-cell lymphocytes in serum samples and by monitoring the duration of transplant organ acceptance. It is expected that candidates receiving an effective amount of the implantable material of the present invention will display a reduction in proliferation of lymphocytes and/or an increase in the duration of transplant organ acceptance.

Treatment of Autoimmune Disease:

A population of patients diagnosed with an autoimmune disease will be identified. The population will be divided into two groups, one of which will receive an effective amount of the implantable material of the present invention. Reduction of and/or amelioration of an autoimmune response and/or an inflammatory response will be monitored over time by evaluating the proliferation of T-cell lymphocytes and B-cell lymphocytes in serum samples and by monitoring the intensity and duration of symptoms associated with the autoimmune disease. It is expected that candidates receiving an effective amount of the implantable material of the present invention will display a reduction in proliferation of lymphocytes and/or a reduction in the frequency and/or intensity of symptoms.

What we claim is:

1. A method of treating a recipient of a cell, tissue or organ from a donor, the method comprising the steps of:
   administering to the recipient one or more doses of a cell, tissue or organ from a syngeneic or non-syngeneic donor; and
   providing to the recipient an implantable material comprising
   a biocompatible matrix; and,
   endothelial cells anchored or embedded in a 3D matrix,
   wherein the providing step is prior to, coincident with, or subsequent to administration to said recipient of the one or more doses of a cell, tissue or organ from a syngeneic or non-syngeneic donor, and
   wherein said implantable material is delivered locally at a non-luminal site to the recipient in an amount sufficient to systemically modulate the recipient's humoral or cellular immune response to said donor cell, tissue or organ.

2. The method of claim 1, wherein said method modulates a recipient's humoral or cellular immune response to administration of a non-syngeneic donor cell, tissue or organ.

3. The method of claim 1, wherein modulation of the recipient's immune response results in reduced maturation of innate immune cells, wherein said innate immune cells are selected from the group consisting of NK cells, dendritic cells, monocytes, and macrophages.

4. The method of claim 3, wherein modulation of the recipient's immune response results in reduced expression by dendritic cells of HLA-DR, IL 12, Toll-like receptor or CD83; inhibits dendritic cell-induced lymphocyte proliferation; or inhibits proliferation, activation or differentiation of dendritic cells.

5. The method of claim 1, wherein the cells embedded in the matrix are autologous, allogeneic, xenogeneic or genetically-modified variants or any one of the foregoing.

6. A method of treating an individual exposed to an exogenous immunogen, the method comprising the steps of:
    identifying an individual exposed to or likely exposed to an exogenous immunogen; and
    administering to the individual exposed to the exogenous immunogen an implantable material comprising
    a biocompatible matrix; and,
    endothelial cells anchored or embedded in a 3D matrix,
    wherein the administering step is prior to, coincident with, or subsequent to the exogenous immunogen, and
    wherein said implantable material is administered locally at a non-luminal site to said individual exposed to the exogenous immunogen in an amount sufficient to systemically reduce the exposed individual's immune inflammatory reaction resulting from exposure to the exogenous immunogen.

7. The method of claim 6, wherein said exogenous immunogen is naturally occurring.

8. The method of claim 6, wherein said exogenous immunogen is selected from the group consisting of pharmaceutical agents, toxins, surgical implants, infectious agents and chemicals.

9. The method of claim 6, wherein the cells embedded in the matrix are autologous, allogeneic, xenogeneic or genetically-modified variants or any one of the foregoing.

10. The method of claim 1, wherein the cells embedded in the matrix are vascular endothelial cells.

11. The method of claim 6, wherein the cells embedded in the matrix are vascular endothelial cells.

12. The method of claim 1, wherein the cells embedded in the matrix are selected from the group consisting of: progenitor cells, stem cells, non-endothelial cells, and genetically-altered, -engineered or -modified cells.

13. The method of claim 6, wherein the cells embedded in the matrix are selected from the group consisting of: progenitor cells, stem cells, non-endothelial cells, and genetically-altered, -engineered or -modified cells.

* * * * *